(12) United States Patent
Pecor et al.

(10) Patent No.: US 7,438,699 B2
(45) Date of Patent: Oct. 21, 2008

(54) QUICK PRIMING CONNECTORS FOR BLOOD CIRCUIT

(75) Inventors: Robert Pecor, Aliso Viejo, CA (US); Michael Scott, Lake Forest, CA (US)

(73) Assignee: Orqis Medical Corporation, Lake Forest, CA (US)

( * ) Notice: Subject to any disclaimer, the term of this patent is extended or adjusted under 35 U.S.C. 154(b) by 330 days.

(21) Appl. No.: 11/370,225

(22) Filed: Mar. 6, 2006

(65) Prior Publication Data

US 2007/0208290 A1 Sep. 6, 2007

(51) Int. Cl.
*A61M 37/00* (2006.01)
*A61M 25/16* (2006.01)

(52) U.S. Cl. .................. 604/6.16; 604/533; 604/905

(58) Field of Classification Search ............... 604/6.16, 604/533, 264, 411, 415, 905
See application file for complete search history.

(56) References Cited

U.S. PATENT DOCUMENTS

| 852,237 | A | | 4/1907 | Nielsen |
|---|---|---|---|---|
| 3,156,491 | A | | 11/1964 | Jackson et al. |
| 4,303,263 | A | | 12/1981 | Legris |
| 4,531,937 | A | | 7/1985 | Yales |
| 4,714,461 | A | | 12/1987 | Gabel |
| 4,758,225 | A | | 7/1988 | Cox et al. |
| 4,759,751 | A | | 7/1988 | Gabel et al. |
| 4,816,221 | A | * | 3/1989 | Harvey et al. .................. 422/25 |
| 4,826,477 | A | | 5/1989 | Adams |
| 4,966,586 | A | | 10/1990 | Vaillencourt |
| 5,122,123 | A | | 6/1992 | Vaillancourt |
| 5,312,352 | A | | 5/1994 | Leschinsky et al. |
| 5,360,395 | A | | 11/1994 | Utterberg |
| 5,439,448 | A | | 8/1995 | Leschinsky et al. |
| 5,776,116 | A | * | 7/1998 | Lopez et al. ................ 604/533 |
| 5,833,674 | A | * | 11/1998 | Turnbull et al. ............. 604/533 |
| 6,050,987 | A | * | 4/2000 | Rosenbaum ................ 604/533 |
| 6,221,065 | B1 | | 4/2001 | Davis |
| 6,471,674 | B1 | | 10/2002 | Emig et al. |
| 6,699,219 | B2 | | 3/2004 | Emig et al. |
| 6,770,049 | B2 | * | 8/2004 | Ludt et al. ................. 604/6.16 |
| 2002/0161322 | A1 | | 10/2002 | Utterberg et al. |
| 2004/0222139 | A1 | | 11/2004 | Brugger et al. |

FOREIGN PATENT DOCUMENTS

| WO | WO 01/32256 | 5/2001 |
|---|---|---|
| WO | WO 2005/099810 | 10/2005 |
| WO | WO 2007/049092 | 5/2007 |

* cited by examiner

*Primary Examiner*—Leslie R Deak
(74) *Attorney, Agent, or Firm*—Knobbe, Martens, Olson & Bear, LLP

(57) ABSTRACT

A connector system is provided for use in priming a fluid circuit. The system includes a first connector and a second connector. The first connector is configured to couple with one end of a conduit. The first connector has a gas permeable membrane, a main lumen extending from the gas permeable membrane, and a second lumen. The second lumen has a first end configured to couple with a fluid source and a second end in fluid communication with the main lumen. The second connector is configured to couple with an end of a cannula. The second connector has an end configured to be inserted through the gas permeable membrane into the first connector, whereby fluid communication can be established between the main lumen of the first connector and the cannula lumen.

29 Claims, 23 Drawing Sheets

QUICK PRIMING CONNECTORS FOR BLOOD CIRCUIT

BACKGROUND OF THE INVENTION

1. Field of the Invention

This application is directed to a system and method for removing an unwanted gas or fluid from a fluid circuit and more particularly is directed to removing gas from a blood circuit.

2. Description of the Related Art

Dialysis and other medical procedures have been implemented to treat blood in patients. In dialysis, blood is removed from and then returned to the patient after being treated. The treatment removes impurities from the blood, a function performed by the kidney in a healthy person. Typically, blood is withdrawn via a first catheter, forced through a filter, and returned to the patient via a second catheter.

Various techniques have been developed to apply these systems in a manner that prevents embolic matter, including gases, from entering patient's blood stream. For example, a technique can be employed where two catheters are connected together. Prior to this connection, the catheters are filled as much as possible at the ends being connected. Then the ends of the two catheters are coupled together. This technique is not optimal at least because it requires spillage of some of the fluid in the catheters to significantly reduce the potential for introduction of embolic matter, e.g., gas. Additionally, this technique usually requires at least two people to fill the catheters and couple them together.

SUMMARY OF THE INVENTION

It would be advantageous to have devices and techniques that enable quickly priming two fluid conveying portions of a fluid circuit. Such priming would enable the two fluid conveying portions to be connected together whereby the risk of introduction of embolic matter or material, e.g., gas, is reduced or eliminated. Preferably such system will be easy to use and will result in minimum spillage of fluids.

In one embodiment, a system for priming a liquid circuit is provided. The system includes a tube assembly and a cannula assembly. The tube assembly includes a tube and a tube connector. The tube connector has a housing with a lumen therethrough having a housing cross-sectional area. The housing also comprising a first port, a membrane extending across the first port, a second port configured to couple with the tube, and a third port configured to couple with a source of liquid. The cannula assembly comprises a cannula and a cannula connector. The cannula includes a first end and a second end configured to couple with a source of liquid to be conveyed in the circuit. The cannula defines a portion of a cannula lumen having a first cross-sectional area. The cannula connector includes a piercing member that defines a portion of the cannula lumen having a second cross-sectional area. The second cross-sectional area is substantially the same as the first cross-sectional area. The piercing member is configured to pierce the membrane upon joining the cannula connector to the tube connector.

In one variation of the system described in the preceding paragraph, the system is for priming a blood-flow circuit coupled with a pump. The system includes a pump tube assembly and a cannula assembly. The pump tube assembly includes a pump tube and a pump tube connector. The pump tube connector has a housing with a lumen therethrough having a housing cross-sectional area. The pump tube connector has a first port, a membrane extending across the first port, a second port configured to couple with the pump tube, and a third port configured to couple with a source of biocompatible liquid. The cannula assembly includes a cannula having a second end configured to couple with a blood vessel.

In another implementation, a method of priming a blood circuit is provided. The blood circuit comprises a pump, a pump tube having a pump tube lumen fluidly coupled with the pump, a gas permeable membrane extending across the pump tube lumen, a cannula having a cannula lumen that extends between a first end and a second end and a piercing structure adjacent to the first end. The method comprises: forcing a biocompatible liquid into the pump tube lumen at a location between the gas permeable membrane and the pump to pressurize the pump tube lumen and to force gas in the pump tube lumen through the membrane; and piercing the membrane with the piercing structure such that the cannula lumen and the pump tube lumen are in fluid communication.

In another embodiment, a connector system for use in priming a fluid circuit is provided. The fluid circuit has a pump, a conduit having a first end coupled with the pump and a second end, a cannula having a first end and a second end configured to fluidly couple with a first fluid source, and a cannula lumen extending between the first and second ends. The system includes a first connector and a second connector. The first connector is configured to couple with the second end of the conduit. The first connector has a gas permeable membrane, a main lumen extending from the gas permeable membrane, and a secondary lumen. The second lumen has a first end configured to couple with a second fluid source and a second end in fluid communication with the main lumen. The second connector is configured to couple with the first end of the cannula. The second connector has an end configured to be inserted through the gas permeable membrane into the first connector, whereby fluid communication can be established between the main lumen of the first connector and the cannula lumen.

One variation of the embodiment set forth in the preceding paragraph involves a connector system for use in priming a blood circuit. In this variation, the cannula has a first end configured to fluidly couple with a blood vessel. The system comprises a first connector and a second connector. The first connector has a lumen that has a first end configured to couple with a source of bio-compatible liquid.

BRIEF DESCRIPTION OF THE DRAWINGS

These and other features and advantages of the invention will now be described with reference to the drawings, which are intended to illustrate and not to limit the invention.

DETAILED DESCRIPTION OF THE PREFERRED EMBODIMENT

Turning now to the drawings provided herein, more detailed descriptions of various embodiments of heart assist systems and cannulae and cannulae connector systems for use therwith are provided below. The connector systems can be used to couple two conduits of a fluid circuit, such as a conduit that can be connected to a pump and a cannula connectable or inertable into a blood vessel. As discussed below in connection with FIGS. 17-23, the liquid circuit primary systems, connector systems, and techniques described below can be applied outside the context of vascular access and medical treatment, for example, these systems and techniques are applicable whenever it is desirable to prime a fluid circuit such that foreign matter, particularly gas, is excluded.

FIGS. 1-16 illustrate some blood supplementation systems with which the priming systems, connectors systems, and priming techniques can be used. Other environments in which the connector system can be deployed include circuits for circulating or conveying biological fluids, such as whole blood, plasma, or other subsets of whole blood, in connection with other treatment techniques.

I. Extracardiac Heart Assist Systems and Methods

A variety of cannulae and cannula assemblies are described herein that can be used in connection with a variety of heart assist systems that supplement perfusion. Such systems preferably are extracardiac in nature. In other words, the systems supplement blood perfusion, without the need to interface directly with the heart and aorta. Thus, the systems can be applied without major invasive surgery. The systems also lessen the hemodynamic burden or workload on the heart by reducing afterload, impedance, and/or left ventricular end diastolic pressure and volume (preload). The systems also advantageously increase peripheral organ perfusion and provide improvement in neurohormonal status. As discussed more fully below, the systems can be applied using one or more cannulae, one or more vascular grafts, and a combination of one or more cannulae and one or more vascular grafts. For systems employing cannula(e), the cannula(e) can be applied through multiple percutaneous insertion sites (sometimes referred to herein as a multi-site application) or through a single percutaneous insertion site (sometimes referred to herein as a single-site application).

A. Heart Assist Systems and Methods Employing Multi-Site Application

Figure 1:
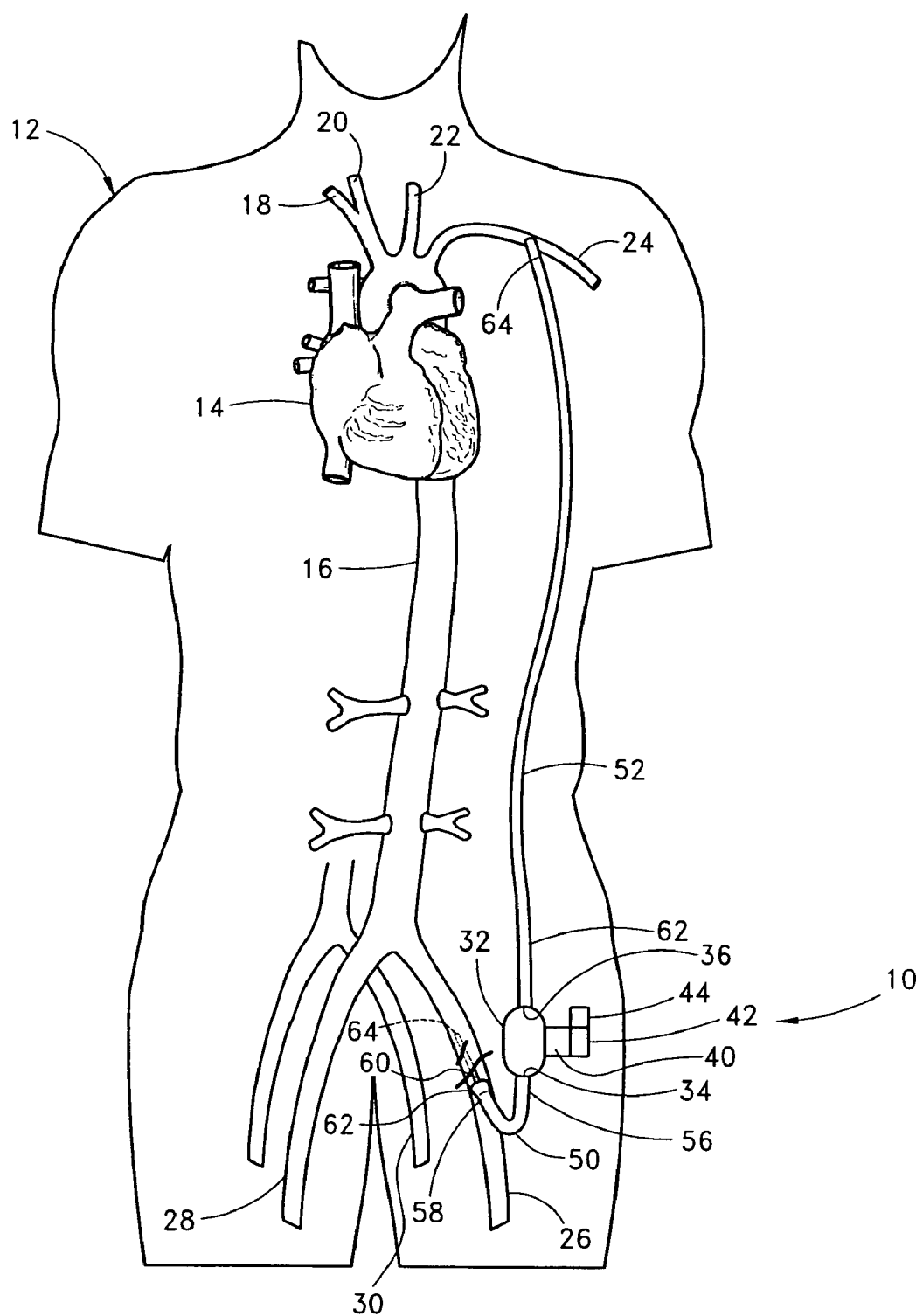
FIG. 1 is a schematic view of one embodiment of a heart assist system having multiple conduits for multi-site application, shown applied to a patient's vascular system.
Figure 2:
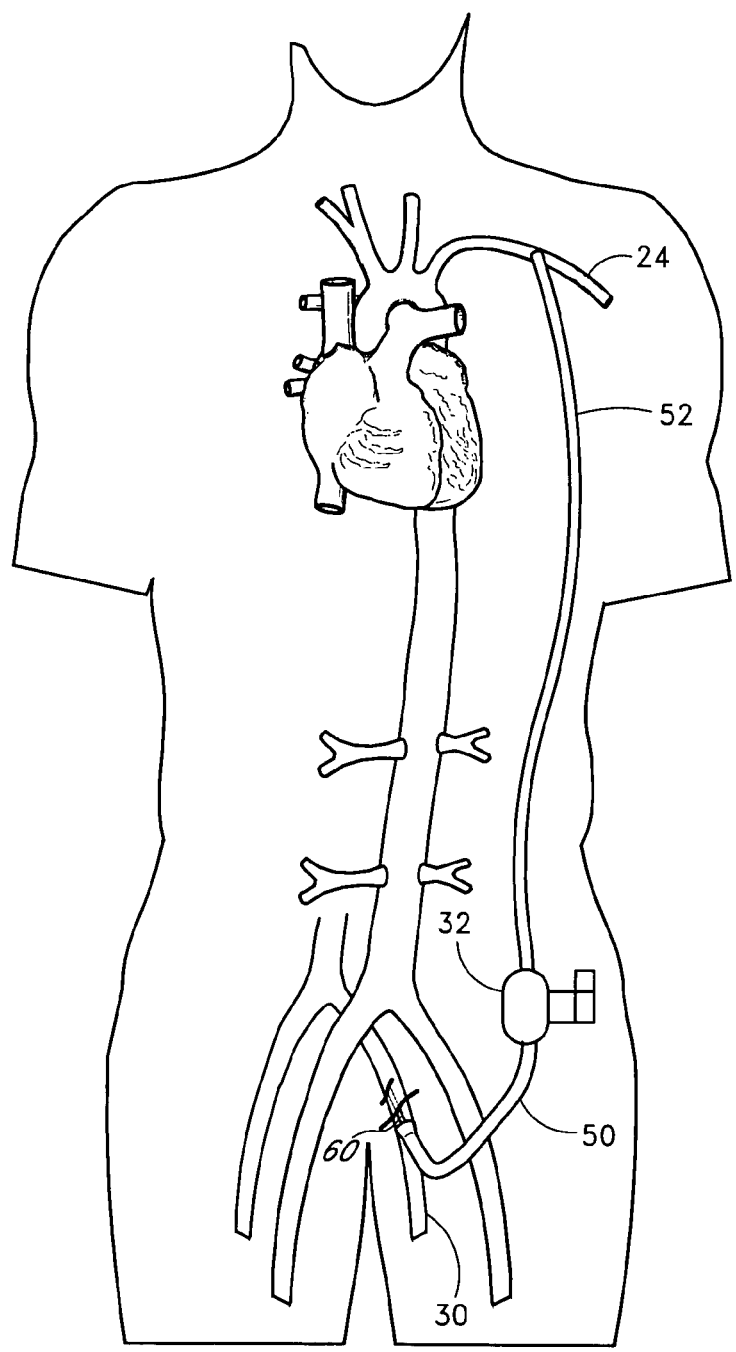
FIG. 2 is a schematic view of another application of the embodiment of FIG. 1.

With reference to FIG. 1, a first embodiment of a heart assist system 10 is shown applied to a patient 12 having an ailing heart 14 and an aorta 16, from which peripheral brachiocephalic blood vessels extend, including the right subclavian artery 18, the right carotid artery 20, the left carotid artery 22, and the left subclavian artery 24. Extending from the descending aorta is another set of peripheral blood vessels, the left and right iliac arteries which transition into the left and right femoral arteries 26, 28, respectively. As is known, each of the arteries 16, 18, 20, 22, 24, 26, and 28 generally conveys blood away from the heart. The vasculature includes a venous system that generally conveys blood to the heart. As will be discussed in more detail below, the heart assist systems described herein can also be applied to non-primary veins, including the left femoral vein 30.

The heart assist system 10 comprises a pump 32, having an inlet 34 and an outlet 36 for connection of conduits thereto. The pump 32 preferably is a rotary pump, either an axial type or a centrifugal type, although other types of pumps may be used, whether commercially-available or customized. The pump 32 preferably is sufficiently small to be implanted subcutaneously and preferably extrathoracically, for example in the groin area of the patient 12, without the need for major invasive surgery. Because the heart assist system 10 is an extracardiac system, no valves are necessary. Any inadvertent backflow through the pump 32 and/or through the inflow conduit would not harm the patient 12.

Regardless of the style or nature chosen, the pump 32 is sized to generate blood flow at subcardiac volumetric rates, less than about 50% of the flow rate of an average healthy heart, although flow rates above that may be effective. Thus, the pump 32 is sized and configured to discharge blood at volumetric flow rates anywhere in the range of 0.1 to 3 liters per minute, depending upon the application desired and/or the degree of need for heart assist. For example, for a patient experiencing advanced congestive heart failure, it may be preferable to employ a pump that has an average subcardiac rate of 2.5 to 3 liters per minute. In other patients, particularly those with minimal levels of heart failure, it may be preferable to employ a pump that has an average subcardiac rate of 0.5 liters per minute or less. In yet other patients it may be preferable to employ a pump that is a pressure wave generator that uses pressure to augment the flow of blood generated by the heart.

In one embodiment, the pump 32 is a continuous flow pump which superimposes continuous blood-flow on the pulsatile aortic blood-flow. In another embodiment, the pump 32 has the capability of synchronous actuation; i.e., it may be actuated in a pulsatile mode, either in copulsating or counterpulsating fashion.

For copulsating action, it is contemplated that the pump 32 would be actuated to discharge blood generally during systole, beginning actuation, for example, during isovolumic contraction before the aortic valve opens or as the aortic valve opens. The pump 32 would be static while the aortic valve is closed following systole, ceasing actuation, for example, when the aortic valve closes.

For counterpulsating actuation, it is contemplated that the pump 32 would be actuated generally during diastole, ceasing actuation, for example, before or during isovolumic contraction. Such an application would permit and/or enhance coronary blood perfusion. In this application, it is contemplated that the pump 32 would be static during the balance of systole after the aortic valve is opened, to lessen the burden against which the heart must pump. The aortic valve being open encompasses the periods of opening and closing, wherein blood is flowing therethrough.

It should be recognized that the designations copulsating and counterpulsating are general identifiers and are not limited to specific points in the patient's heart cycle when the pump 32 begins and discontinues actuation. Rather, they are intended to generally refer to pump actuation in which the pump 32 is actuating, at least in part, during systole and diastole, respectively. For example, it is contemplated that the pump 32 might be activated to be out of phase from true copulsating or counterpulsating actuation described herein, and still be synchronous, depending upon the specific needs of the patient or the desired outcome. One might shift actuation of the pump 32 to begin prior to or after isovolumic contraction or to begin before or after isovolumic relaxation.

Furthermore, the pulsatile pump may be actuated to pulsate asynchronously with the patient's heart. Typically, where the patient's heart is beating irregularly, there may be a desire to pulsate the pump 32 asynchronously so that the perfusion of blood by the heart assist system 10 is more regular and, thus, more effective at oxygenating the organs. Where the patient's heart beats regularly, but weakly, synchronous pulsation of the pump 32 may be preferred.

The pump 32 is driven by a motor 40 and/or other type of drive means and is controlled preferably by a programmable controller 42 that is capable of actuating the pump 32 in pulsatile fashion, where desired, and also of controlling the speed or output of the pump 32. For synchronous control, the patient's heart would preferably be monitored with an EKG in which feedback would be provided the controller 42. The controller 42 is preferably programmed by the use of external means. This may be accomplished, for example, using RF telemetry circuits of the type commonly used within implantable pacemakers and defibrillators. The controller may also be autoregulating to permit automatic regulation of the speed, and/or regulation of the synchronous or asynchronous pulsation of the pump 32, based upon feedback from ambient sensors monitoring parameters, such as pressure or the patient's EKG. It is also contemplated that a reverse-direction pump be utilized, if desired, in which the controller is capable of reversing the direction of either the drive means or the impellers of the pump. Such a pump might be used where it is desirable to have the option of reversing the direction of circulation between two blood vessels.

Power to the motor 40 and the controller 42 may be provided by a power source 44, such as a battery, that is preferably rechargeable by an external induction source (not shown), such as an RF induction coil that may be electromagnetically coupled to the battery to induce a charge therein. Alternative power sources are also possible, including a device that draws energy directly from the patient's body; e.g., the patient's muscles, chemicals or heat. The pump can be temporarily stopped during recharging with no appreciable life threatening effect, because the system only supplements the heart, rather than substituting for the heart.

Figure 16:
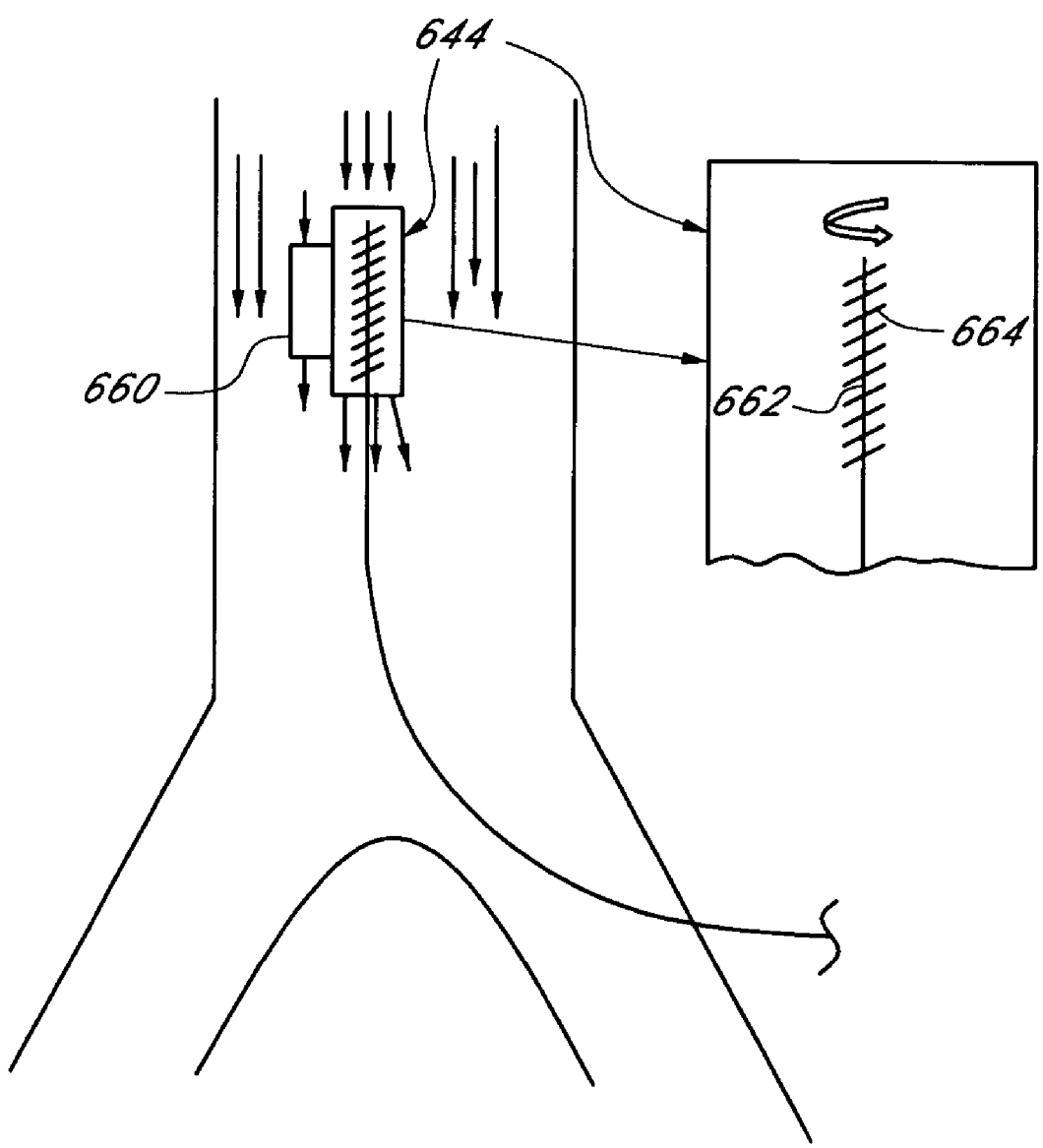
FIG. 16 is a schematic view of a modified embodiment of the heart assist system of FIG. 15 in which an additional conduit is shown adjacent the conduit housing the pump, and in which the pump comprises a shaft-mounted helical thread.

While the controller 42 and power source 44 are preferably pre-assembled to the pump 32 and implanted therewith, it is also contemplated that the pump 32 and motor 40 be implanted at one location and the controller 42 and the power source 44 be implanted in a separate location. In one alternative arrangement, the pump 32 may be driven externally through a percutaneous drive line or cable, as shown in FIG. 16. In another variation, the pump, motor and controller may be implanted and powered by an extracorporeal power source. In the latter case, the power source could be attached to the side of the patient to permit fully ambulatory movement.

The inlet 34 of the pump 32 is preferably connected to an inflow conduit 50 and an outflow conduit 52 to direct blood flow from one peripheral blood vessel to another. Although described as "inflow" and "outflow" conduits, these conduits can convey the blood to the pump 32 as well as away from the pump. The conduits 50, 52 preferably are flexible conduits, as discussed more fully below. The conduits 50, 52 are coupled with the peripheral vessels in different ways in various embodiments of the heart assist system 10. As discussed more fully below, at least one of the conduits 50, 52 can be connected to a peripheral vessel, e.g., as a graft, using an anastomosis connection, and at least one of the conduits 50, 52 can be coupled with the same or another vessel via insertion of a cannula into the vasculature. Also, more than two conduits are used in some embodiments, as discussed below.

The inflow and outflow conduits 50, 52 may be formed from Dacron, Hemashield, Gortex, PVC, polyurethane, PTFE, ePTFE, nylon, or PEBAX materials, although other synthetic materials may be suitable. The inflow and outflow conduits 50, 52 may also comprise biologic materials or pseudobiological (hybrid) materials (e.g., biologic tissue supported on a synthetic scaffold). The inflow and outflow conduits 50, 52 are preferably configured to minimize kinks so blood flow is not meaningfully interrupted by normal movements of the patient or compressed easily from external forces. In some cases, the inflow and/or outflow conduits 50, 52 may come commercially already attached to the pump 32. Where it is desired to implant the pump 32 and the conduits 50, 52, it is preferable that the inner diameter of the conduits 50, 52 be less than 25 mm, although diameters slightly larger may be effective.

In one preferred application, the heart assist system 10 is applied in an arterial-arterial fashion; for example, as a femoral-axillary connection, as is shown in FIG. 1. It should be appreciated by one of ordinary skill in the art that an axillary-femoral connection would also be effective using the embodiments described herein. Indeed, it should be recognized by one of ordinary skill in the art that the present invention might be applied to any of the peripheral blood vessels in the patient. Another application of the heart assist system 10 couples the conduits 50, 52 with the same non-primary vessel in a manner similar to the application shown in FIG. 8 and discussed below.

Figure 6:
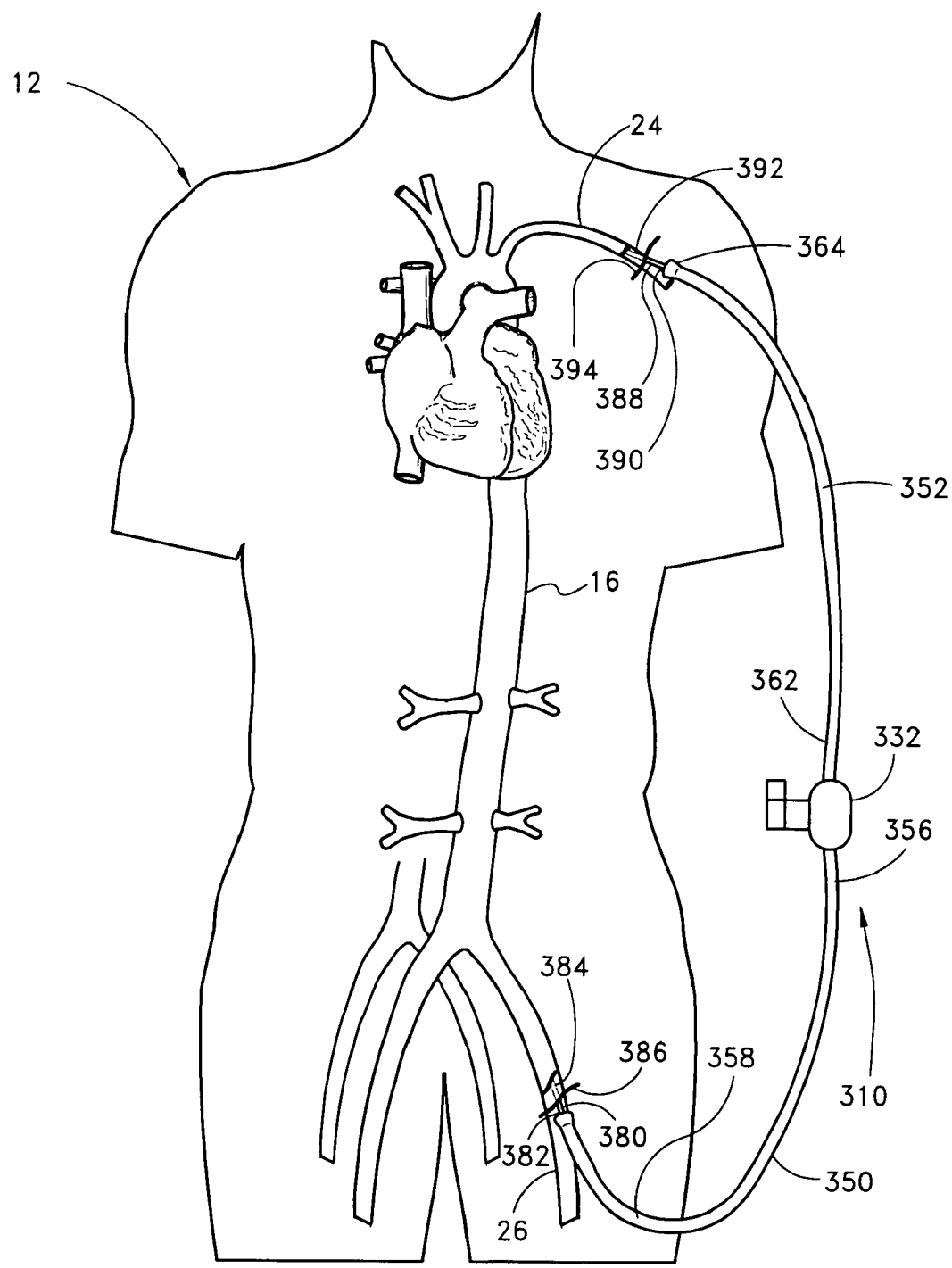
FIG. 6 is a schematic view of another embodiment of a heart assist system having multiple conduits for multi-site application, shown applied to a patient's vascular system.

FIG. 1 shows that the inflow conduit 50 has a first end 56 that connects with the inlet 34 of the pump 32 and a second end 58 that is coupled with a first non-primary blood vessel (e.g., the left femoral artery 26) by way of an inflow cannula 60. The inflow cannula 60 has a first end 62 and a second end 64. The first end 62 is sealably connected to the second end 58 of the inflow conduit 50. The second end 64 is inserted into the blood vessel (e.g., the left femoral artery 26). Although shown as discrete structures in FIG. 1, one skilled in the art would recognize that the inflow conduit 50 and the cannula 60 may be unitary in construction. Any suitable technique or structure can be used to couple the inflow conduit 50 and the cannula 60 together. Various embodiments of suitable structures and techniques for connecting the second end 58 of the inflow conduit 50 to the cannula 60 where these components are separable are discussed in detail below in connection with FIGS. 17-23.

Where the conduit 50 is at least partially extracorporeal, the inflow cannula 60 also may be inserted through a surgical opening (e.g., as shown in FIG. 6 and described in connection therewith) or percutaneously, with or without an introducer sheath (not shown). In other applications, the inflow cannula 60 could be inserted into the right femoral artery or any other peripheral artery.

FIG. 1 shows that the outflow conduit 52 has a first end 66 that connects to the outlet 36 of the pump 32 and a second end 68 that connects with a second peripheral blood vessel, preferably the left subclavian artery 24 of the patient 12, although the right axillary artery, or any other peripheral artery, would be acceptable. In one application, the connection between the outflow conduit 52 and the second blood vessel is via an end-to-side anastomosis, although a side-to-side anastomosis connection might be used mid-stream of the conduit where the outflow conduit were connected at its second end to yet another blood vessel or at another location on the same blood vessel (neither shown). Preferably, the outflow conduit 52 is attached to the second blood vessel at an angle that results in the predominant flow of blood out of the pump 32 proximally toward the aorta 16 and the heart 14, such as is shown in FIG. 1, while still maintaining sufficient flow distally toward the hand to prevent limb ischemia.

In another embodiment, the inflow conduit 50 is connected to the first blood vessel via an end-to-side anastomosis, rather than via the inflow cannula 60. The inflow conduit 50 could also be coupled with the first blood vessel via a side-to-side anastomosis connection mid-stream of the conduit where the inflow conduit were connected at its second end to an additional blood vessel or at another location on the same blood vessel (neither shown). Further details of these arrangements and other related applications are described in U.S. Pat. No. 6,889,082, issued May 3, 2005, the entire contents of which is hereby incorporated by reference in its entirety and made a part of this specification.

In another embodiment, the outflow conduit 52 also is coupled with the second blood vessel via a cannula, as shown in FIG. 6. This connection may be achieved in a manner similar to that shown in FIG. 1 in connection with the first blood vessel.

It is preferred that application of the heart assist system 10 to the peripheral or non-primary blood vessels be accomplished subcutaneously; e.g., at a shallow depth just below the skin or first muscle layer so as to avoid major invasive surgery. It is also preferred that the heart assist system 10 be applied extrathoracically to avoid the need to invade the patient's chest cavity. Where desired, the entire heart assist system 10 may be implanted within the patient 12, either extravascularly, e.g., as in FIG. 1, or at least partially intravascularly, e.g., as in FIGS. 14-16.

In the case of an extravascular application, the pump 32 may be implanted, for example, into the groin area, with the inflow conduit 50 fluidly connected subcutaneously to, for example, the femoral artery 26 proximate the pump 32. The outflow conduit would be tunneled subcutaneously through to, for example, the left subclavian artery 24. In an alternative arrangement, the pump 32 and associated drive and controller could be temporarily fastened to the exterior skin of the patient, with the inflow and outflow conduits 50, 52 connected percutaneously. In either case, the patient may be ambulatory without restriction of tethered lines.

While the heart assist system 10 and other heart assist systems described herein may be applied to create an arterial-arterial flow path, given the nature of the heart assist systems, i.e., supplementation of circulation to meet organ demand, a venous-arterial flow path may also be used. For example, with reference to FIG. 2, one application of the heart assist system 10 couples the inflow conduit 50 with a non-primary vein of the patient 12, such as the left femoral vein 30. In this arrangement, the outflow conduit 50 may be fluidly coupled with one of the peripheral arteries, such as the left subclavian artery 24. Arterial-venous arrangements are contemplated as well. In those venous-arterial cases where the inflow is connected to a vein and the outflow is connected to an artery, the pump 32 should be sized to permit flow sufficiently small so that oxygen-deficient blood does not rise to unacceptable levels in the arteries. It should be appreciated that the connections to the non-primary veins could be by one or more approach described above for connecting to a non-primary artery. It should also be appreciated that the present invention could be applied as a venous-venous flow path, wherein the inflow and outflow are connected to separate peripheral veins. In addition, an alternative embodiment comprises two discrete pumps and conduit arrangements, one being applied as a venous-venous flow path, and the other as an arterial-arterial flow path.

When venous blood is mixed with arterial blood either at the inlet of the pump or the outlet of the pump the ratio of venous blood to arterial blood should be controlled to maintain an arterial saturation of a minimum of 80% at the pump inlet or outlet. Arterial saturation can be measured and/or monitored by pulse oximetry, laser doppler, colorimetry or other methods used to monitor blood oxygen saturation. The venous blood flow into the system can then be controlled by regulating the amount of blood allowed to pass through the conduit from the venous-side connection.

Figure 3:
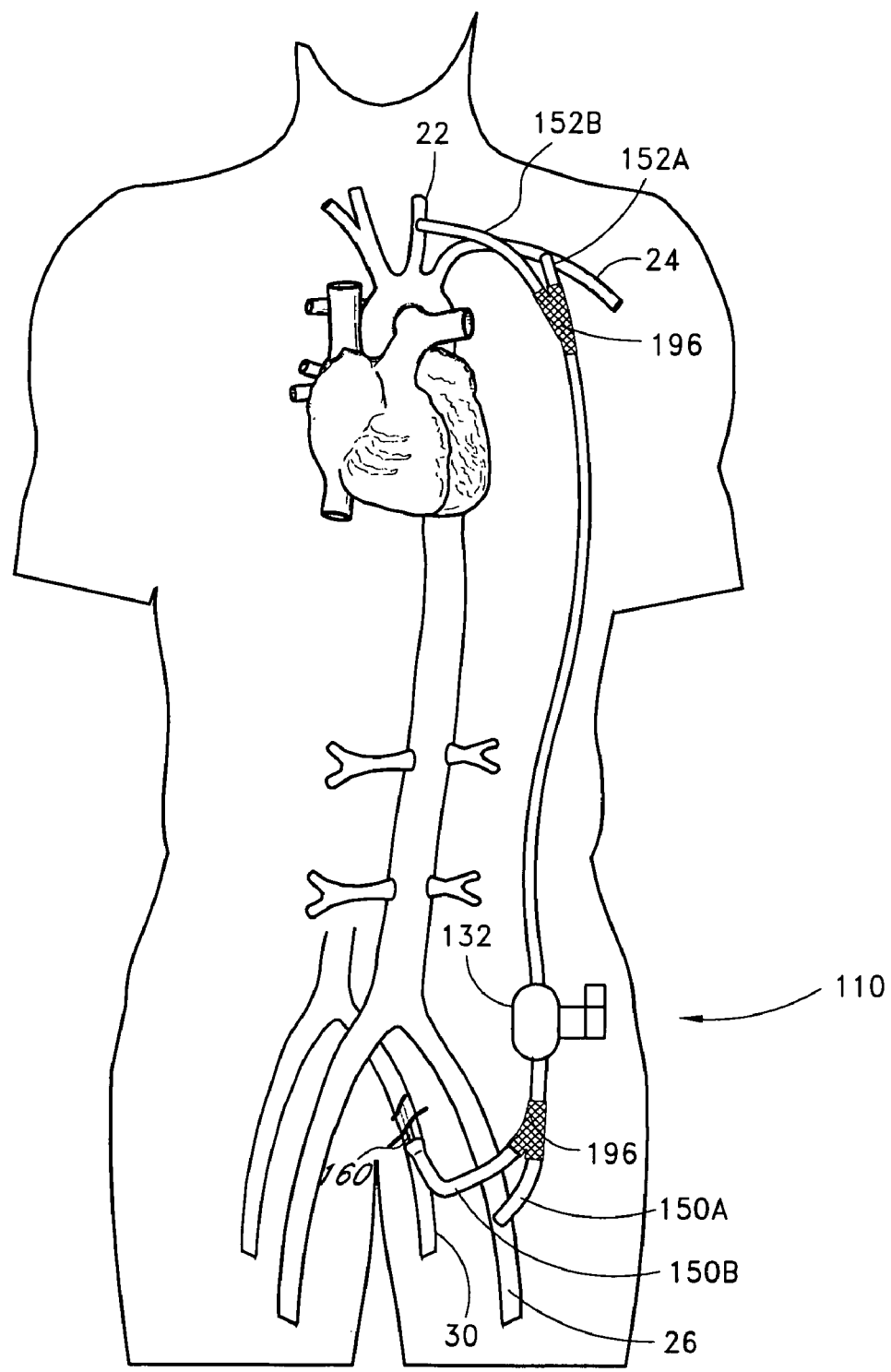
FIG. 3 is a schematic view of another embodiment of a heart assist system having multiple conduits for multi-site application wherein each of the conduits is applied to more than one vessel, shown applied to a patient's vascular system.

FIG. 3 shows another embodiment of a heart assist system 110 applied to the patient 12. For example, the heart assist system 110 includes a pump 132 in fluid communication with a plurality of inflow conduits 150A, 150B and a plurality of outflow conduits 152A, 152B. Each pair of conduits converges at a generally Y-shaped convergence 196 that converges the flow at the inflow end and diverges the flow at the outflow end. Each conduit may be connected to a separate peripheral blood vessel, although it is possible to have two connections to the same blood vessel at remote locations. In one arrangement, all four conduits are connected to peripheral arteries. In another arrangement, one or more of the conduits could be connected to veins. In the arrangement of FIG. 3, the inflow conduit 150A is connected to the left femoral artery 26 while the inflow conduit 150B is connected to the left femoral vein 30. The outflow conduit 152A is connected to the left subclavian artery 24 while the outflow conduit 152B is connected to the left carotid artery 22. Preferably at least one of the conduits 150A, 150B, 152A, and 152B is coupled with a corresponding vessel via a cannula. In the illustrated embodiment, the inflow conduit 150B is coupled with the left femoral vein 30 via a cannula 160. The cannula 160 is coupled to the vessel in a manner similar to that shown in FIG. 2 and described in connection with the cannula 60. The cannula 160 can be coupled with one or more of the conduits 150A, 150B, 152A, 152B using any suitable technique or structure such as any of those discussed below in connection with FIGS. 17-23.

The connections of any or all of the conduits of the system 110 to the blood vessels may be via an anastomosis connection or via a connector, as described below in connection with FIG. 4. In addition, the embodiment of FIG. 3 may be applied to any combination of peripheral blood vessels that would best suit the patient's condition. For example, it may be desired to have one inflow conduit and two outflow conduits or vice versa. It should be noted that more than two conduits may be used on the inflow or outflow side, where the number of inflow conduits is not necessarily equal to the number of outflow conduits.

It is contemplated that, where an anastomosis connection is not desired, a connector may be used to connect at least one of the inflow conduit and the outflow conduit to a peripheral blood vessel. With reference to FIG. 4, an embodiment of a heart assist system 210 is shown, wherein an outflow conduit 252 is connected to a non-primary blood vessel, e.g., the left subclavian artery 24, via a connector 268 that comprises a three-opening fitting. In one embodiment, the connector 268 comprises an intra-vascular, generally T-shaped fitting 270 having a proximal end 272 (relative to the flow of blood in the left axillary artery and therethrough), a distal end 274, and an angled divergence 276 permitting connection to the outflow conduit 252 and the left subclavian artery 24. The proximal and distal ends 274, 276 of the fittings 272 permit connection to the blood vessel into which the fitting is positioned, e.g., the left subclavian artery 24. The angle of divergence 276 of the fittings 272 may be 90 degrees or less in either direction from the axis of flow through the blood vessel, as optimally selected to generate the needed flow distally toward the hand to prevent limb ischemia, and to insure sufficient flow and pressure toward the aorta to provide the circulatory assistance and workload reduction needed while minimizing or avoiding endothelial damage to the blood vessel. In another embodiment, the connector 268 is a sleeve (not shown) that surrounds and attaches to the outside of the non-primary blood vessel where, within the interior of the sleeve, a port to the blood vessel is provided to permit blood flow from the outflow conduit 252 when the conduit 252 is connected to the connector 268.

Figure 5:
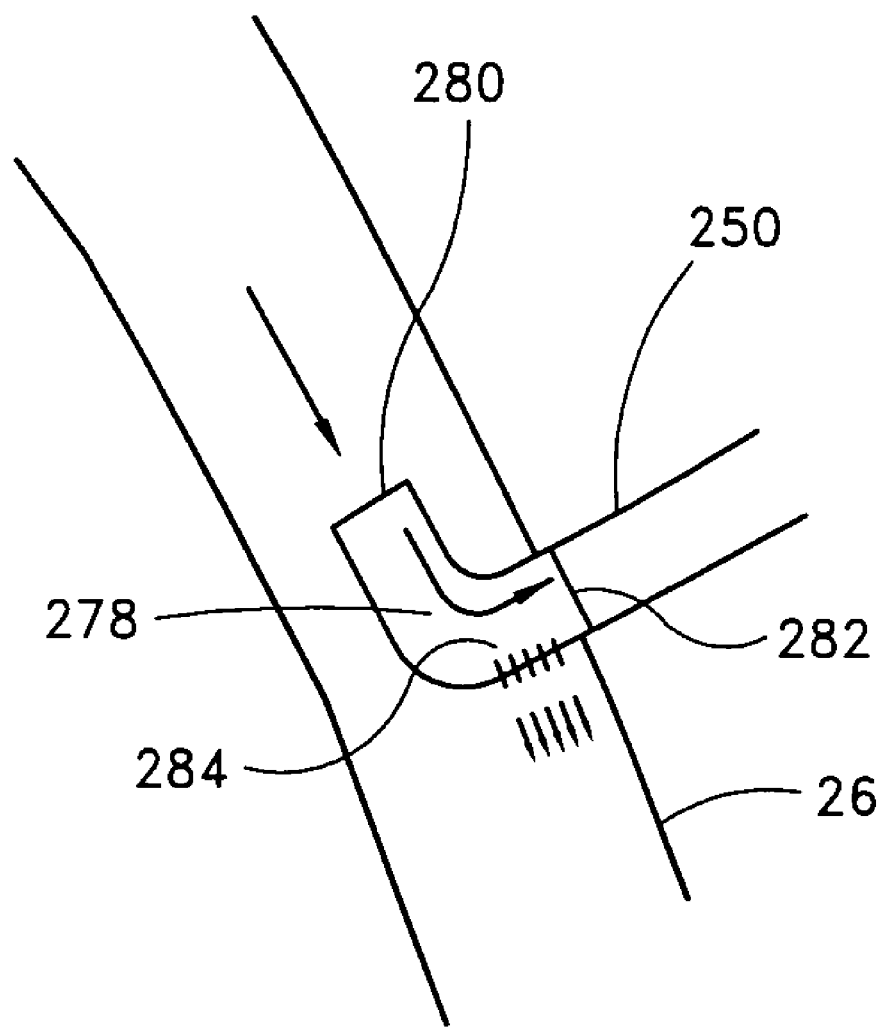
FIG. 5 is a schematic view of an L-shaped connector coupled with an inflow conduit, shown inserted within a blood vessel.

Other types of connectors having other configurations are contemplated that may avoid the need for an anastomosis connection or that permit connection of the conduit(s) to the blood vessel(s). For example, it is contemplated that an L-shaped connector be used if it is desired to withdraw blood more predominantly from one direction of a peripheral vessel or to direct blood more predominantly into a peripheral vessel. Referring to FIG. 5, the inflow conduit 250 is fluidly connected to a peripheral vessel, for example, the left femoral artery 26, using an L-shaped connector 278. Of course the system 210 could be configured so that the outflow conduit 252 is coupled to a non-primary vessel via the L-shaped connector 278 and the inflow conduit 250 is coupled via a cannula, as shown in FIG. 3. The L-shaped connector 278 has an inlet port 280 at a proximal end and an outlet port 282 through which blood flows into the inflow conduit 250. The L-shaped connector 278 also has an arrangement of holes 284 within a wall positioned at a distal end opposite the inlet port 280 so that some of the flow drawn into the L-shaped connector 278 is diverted through the holes 284, particularly downstream of the L-shaped connector 278, as in this application. A single hole 284 in the wall could also be effective, depending upon size and placement. The L-shaped connector 278 may be a deformable L-shaped catheter percutaneously applied to the blood vessel or, in an alternative embodiment, be connected directly to the walls of the blood vessel for more long term application. By directing some blood flow downstream of the L-shaped connector 278 during withdrawal of blood from the vessel, ischemic damage downstream from the connector may be avoided. Such ischemic damage might otherwise occur if the majority of the blood flowing into the L-shaped connector 278 were diverted from the blood vessel into the inflow conduit 252. It is also contemplated that a connection to the blood vessels might be made via a cannula, wherein the cannula is implanted, along with the inflow and outflow conduits.

One advantage of discrete connectors manifests in their application to patients with chronic CHF. A connector eliminates a need for an anastomosis connection between the conduits 250, 252 and the peripheral blood vessels where it is desired to remove and/or replace the system more than one time. The connectors could be applied to the first and second blood vessels semi-permanently, with an end cap applied to the divergence for later quick-connection of the present invention system to the patient. In this regard, a patient might experience the benefit of the heart assist systems described herein periodically, without having to reconnect and redisconnect the conduits 250, 252 from the blood vessels via an anastomosis procedure each time. Each time it is desired to implement any of the embodiments of the heart assist system, the end caps would be removed and a conduit attached to the connector(s) quickly.

Figure 4:
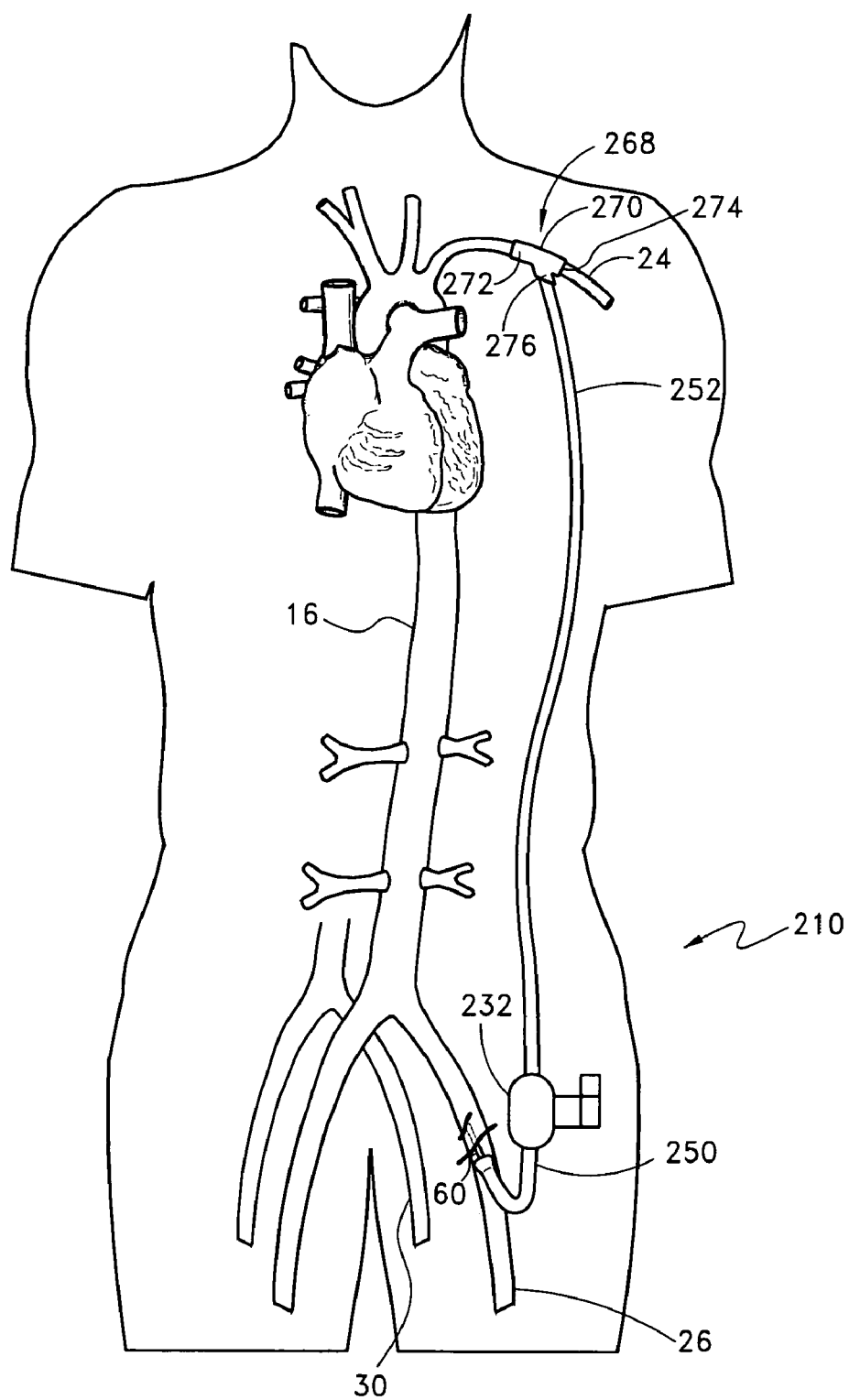
FIG. 4 is a schematic view of another embodiment of a heart assist system having multiple conduits for multi-site application and employing a connector with a T-shaped fitting, shown applied to a patient's vascular system.

In the preferred embodiment of the connector 268, the divergence 276 is oriented at an acute angle significantly less than 90 degrees from the axis of the T-shaped fitting 270, as shown in FIG. 4, so that a majority of the blood flowing through the outflow conduit 252 into the blood vessel (e.g., left subclavian artery 24) flows in a direction proximally toward the heart 14, rather than in the distal direction. In an alternative embodiment, the proximal end 272 of the T-shaped fitting 270 may have a diameter larger than the diameter of the distal end 274, without need of having an angled divergence, to achieve the same result.

With or without a connector, with blood flow directed proximally toward the aorta 16, the result may be concurrent flow down the descending aorta, which will result in the reduction of afterload, impedance, and/or reducing left ventricular end diastolic pressure and volume (preload). Thus, the heart assist systems described herein may be applied so to reduce the afterload on the patient's heart, permitting at least partial if not complete CHF recovery, while supplementing blood circulation. Concurrent flow depends upon the phase of operation of the pulsatile pump and the choice of second blood vessel to which the outflow conduit is connected.

Figure 7:
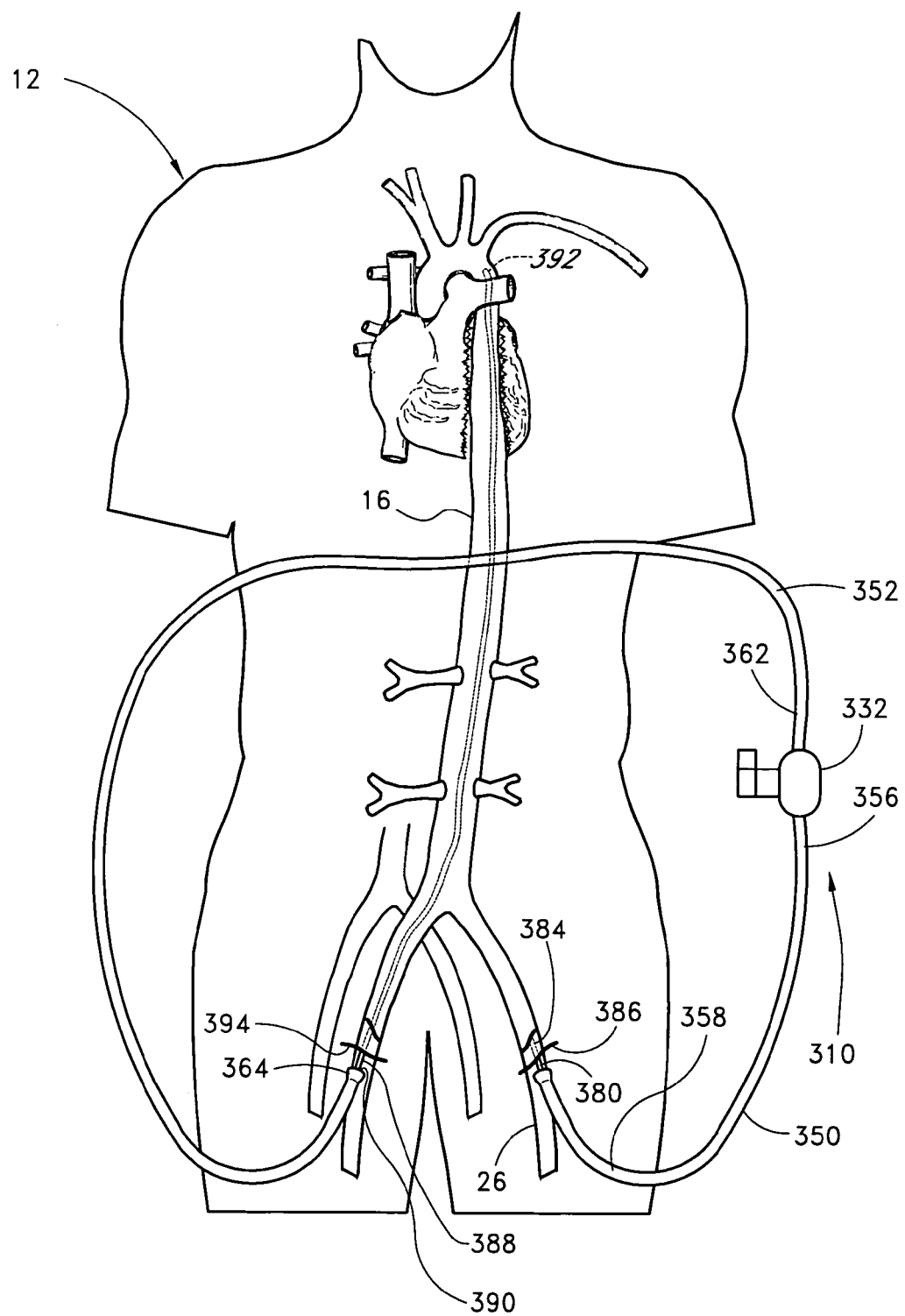
FIG. 7 is a schematic view of another application of the embodiment of FIG. 6, shown applied to a patient's vascular system.

A partial external application of the heart assist systems is contemplated where a patient with heart failure is suffering an acute decompensation episode; i.e., is not expected to last long, or is in the earlier stages of heart failure (where the patient is in New York Heart Association Classification (NYHAC) functional classes II or III). With reference to FIGS. 6 and 7, another embodiment of a heart assist system 310 is applied percutaneously to a patient 312 to connect two non-primary blood vessels wherein a pump 332 and its associated driving means and controls are employed extracorporeally. The pump 332 has an inflow conduit 350 and an outflow conduit 352 associated therewith for connection to two non-primary blood vessels. The inflow conduit 350 has a first end 356 and a second end 358 wherein the second end 358 is connected to a first non-primary blood vessel (e.g., femoral artery 26) by way of an inflow cannula 380. The inflow cannula 380 has a first end 382 sealably connected to the second end 358 of the inflow conduit 350. The inflow cannula 380 also has a second end 384 that is inserted through a surgical opening 386 or an introducer sheath (not shown) and into the blood vessel (e.g., the left femoral artery 26).

Similarly, the outflow conduit 352 has a first end 362 and a second end 364 wherein the second end 364 is connected to a second non-primary blood vessel (e.g., the left subclavian artery 24, as shown in FIG. 6, or the right femoral artery 28, as shown in FIG. 7) by way of an outflow cannula 388. Like the inflow cannula 380, the outflow cannula 388 has a first end 390 sealably connected to the second end 364 of the outflow conduit 352. The outflow cannula 388 also has a second end 392 that is inserted through surgical opening 394 or an introducer sheath (not shown) and into the second blood vessel (e.g., the left subclavian artery 24 or the right femoral artery 28). The cannulae 380 and 388 can take any suitable form and can be coupled with the conduits 350, 352 in any suitable manner, such as by using any of the structures or techniques discussed below in connection with FIGS. 17-23.

As shown in FIG. 7, the second end 392 of the outflow cannula 388 may extend well into the aorta 16 of the patient 12, for example, proximal to the left subclavian artery. If desired, it may also terminate within the left subclavian artery or the left axillary artery, or in other blood vessels, such as the mesenteric or renal arteries (not shown), where in either case, the outflow cannula 388 has passed through at least a portion of a primary artery (in this case, the aorta 16). Also, if desired, blood drawn into the extracardiac system 310 described herein may originate from the descending aorta (or an artery branching therefrom) and be directed into a blood vessel that is neither the aorta nor pulmonary artery. By use of a percutaneous application, the heart assist system 310 may be applied temporarily without the need to implant any aspect thereof or to make anastomosis connections to the blood vessels.

An alternative variation of the embodiment of FIG. 6 may be used where it is desired to treat a patient periodically, but for short periods of time each occasion and without the use of special connectors. With this variation, it is contemplated that the second ends of the inflow and outflow conduits 350, 352 be more permanently connected to the associated blood vessels via, for example, an anastomosis connection, wherein a portion of each conduit proximate to the blood vessel connection is implanted percutaneously with a removable cap enclosing the externally-exposed first end (or an intervening end thereof) of the conduit external to the patient. When it is desired to provide a circulatory flow path to supplement blood flow, the removable cap on each exposed percutaneously-positioned conduit could be removed and the pump (or the pump with a length of inflow and/or outflow conduit attached thereto) inserted between the exposed percutaneous conduits. In this regard, a patient may experience the benefit of the present invention periodically, without having to reconnect and redisconnect the conduits from the blood vessels each time.

Figure 8:
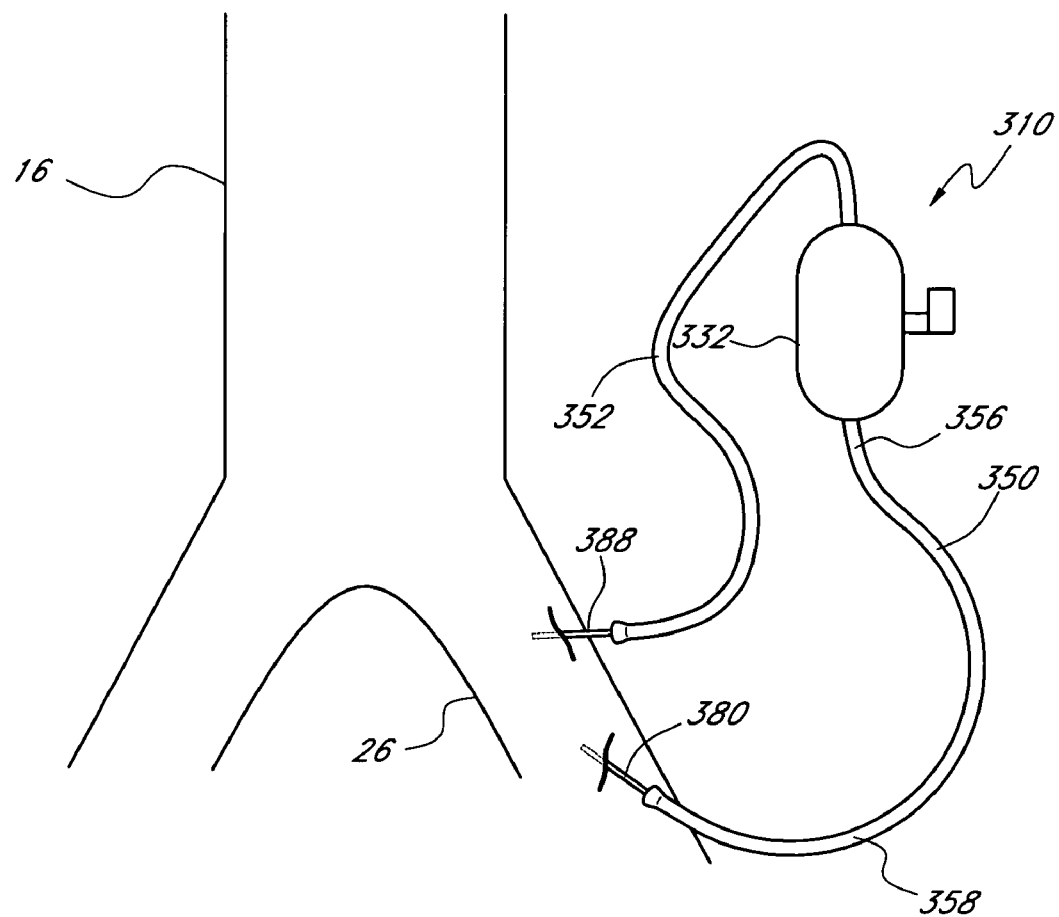
FIG. 8 is a schematic view of another application of the embodiment of FIG. 6, shown applied to a patient's vascular system.

Specific methods of applying this alternative embodiment may further comprise coupling the inflow conduit 352 upstream of the outflow conduit 350 (as shown in FIG. 8), although the reverse arrangement is also contemplated. It is also contemplated that either the cannula 380 coupled with the inflow conduit 350 or the cannula 388 coupled with the outflow conduit 352 may extend through the non-primary blood vessel to a second blood vessel (e.g., through the left femoral artery 26 to the aorta 16 proximate the renal branch) so that blood may be directed from the non-primary blood vessel to the second blood or vice versa.

Figure 9:
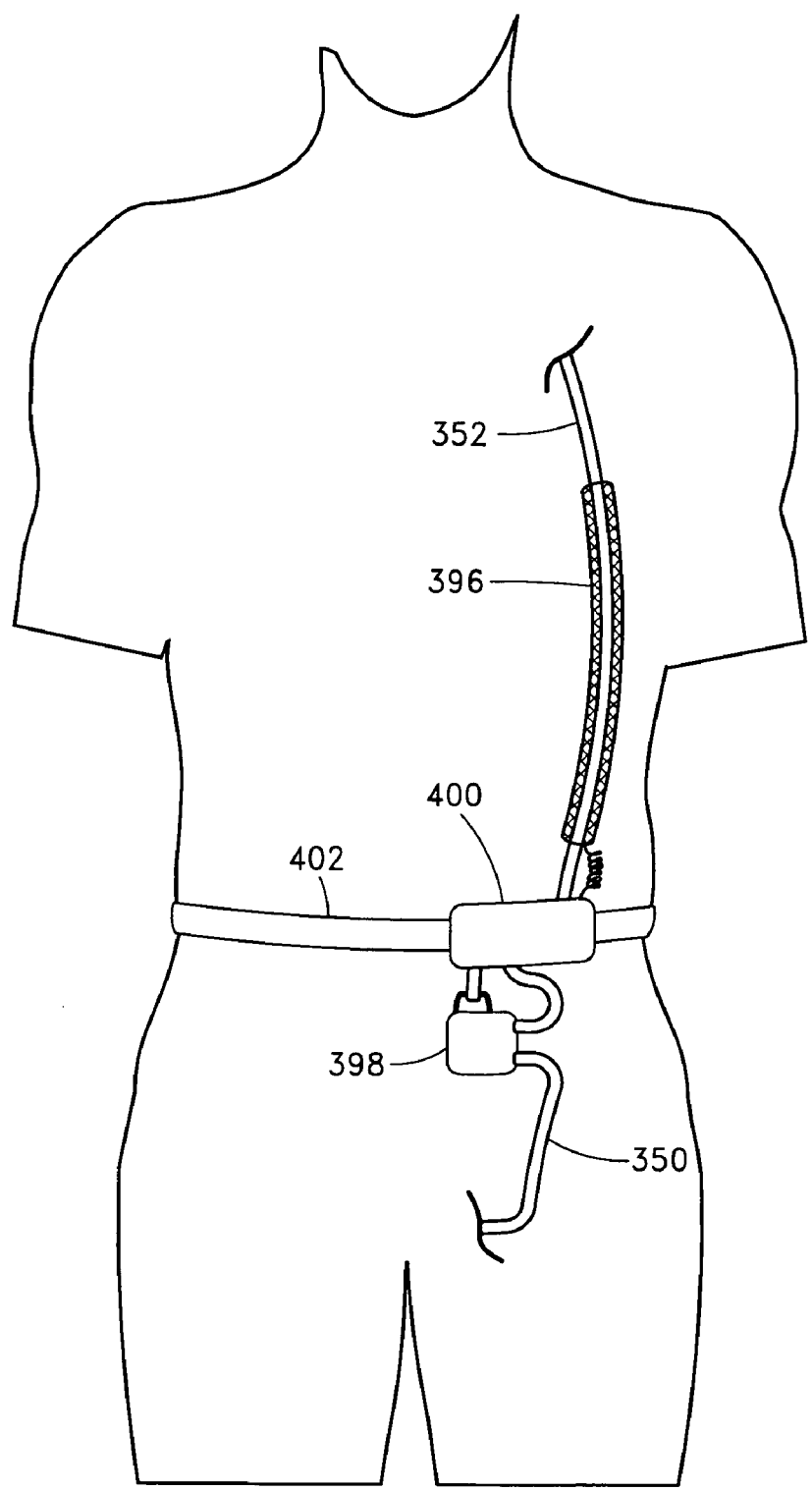
FIG. 9 is a schematic view of another embodiment of a heart assist system having multiple conduits for multi-site application, a reservoir, and a portable housing for carrying a portion of the system directly on the patient.

It is contemplated that a means for minimizing the loss of thermal energy in the patient's blood be provided where any of the heart assist systems described herein are applied extracorporeally. Such means for minimizing the loss of thermal energy may comprise, for example, a heated bath through which the inflow and outflow conduits pass or, alternatively, thermal elements secured to the exterior of the inflow and outflow conduits. Referring to FIG. 9, one embodiment comprises an insulating wrap 396 surrounding the outflow conduit 352 having one or more thermal elements passing therethrough. The elements may be powered, for example, by a battery (not shown). One advantage of thermal elements is that the patient may be ambulatory, if desired. Other means that are known by persons of ordinary skill in the art for ensuring that the temperature of the patient's blood remains at acceptable levels while traveling extracorporeally are also contemplated.

If desired, the present inventive system may further comprise a reservoir that is either contained within or in fluid communication with the inflow conduit. This reservoir is preferably made of materials that are nonthrombogenic. Referring to FIG. 9, a reservoir 398 is positioned fluidly in line with the inflow conduit 350. The reservoir 398 serves to sustain adequate blood in the system when the pump demand exceeds momentarily the volume of blood available in the peripheral blood vessel in which the inflow conduit resides until the pump output can be adjusted. The reservoir 398 reduces the risk of excessive drainage of blood from the peripheral blood vessel, which may occur when cardiac output falls farther than the already diminished baseline level of cardiac output, or when there is systemic vasodilation, as can occur, for example, with septic shock. It is contemplated that the reservoir 398 would be primed with an acceptable solution, such as saline, when the present system is first applied to the patient.

As explained above, one of the advantages of several embodiments of the heart assist system is that such systems permit the patient to be ambulatory. If desired, the systems may be designed portably so that it may be carried directly on the patient. Referring to FIG. 9, this may be accomplished through the use of a portable case 400 with a belt strap 402 to house the pump, power supply and/or the controller, along with certain portions of the inflow and/or outflow conduits, if necessary. It may also be accomplished with a shoulder strap or other techniques, such as a backpack or a fanny pack, that permit effective portability. As shown in FIG. 9, blood is drawn through the inflow conduit 350 into a pump contained within the portable case 400, where it is discharged into the outflow conduit 352 back into the patient.

B. Heart Assist Systems and Methods Employing Single-Site Application

As discussed above, heart assist systems can be applied to a patient through a single cannulation site. Such single-site systems can be configured with a pump located outside the vasculature of a patient, e.g., as extravascular pumping systems, inside the vasculature of the patient, e.g., as intravascular systems, or a hybrid thereof, e.g., partially inside and partially outside the vasculature of the patient.

1. Single-Site Application of Extravascular Pumping Systems

Figure 10:
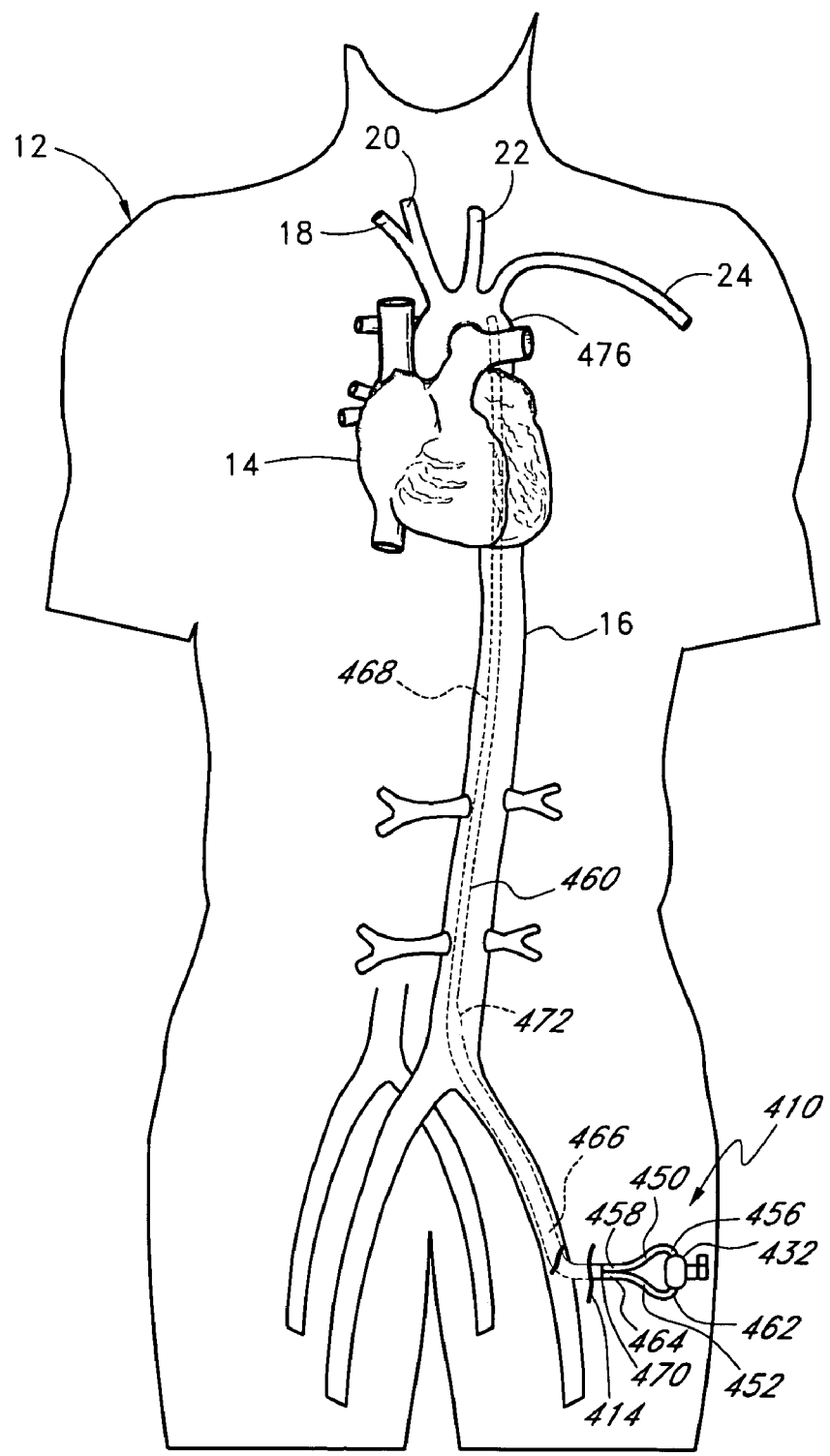
FIG. 10 is a schematic view of another embodiment of a heart assist system having a multilumen cannula for single-site application, shown applied to a patient's vascular system.
Figure 11:
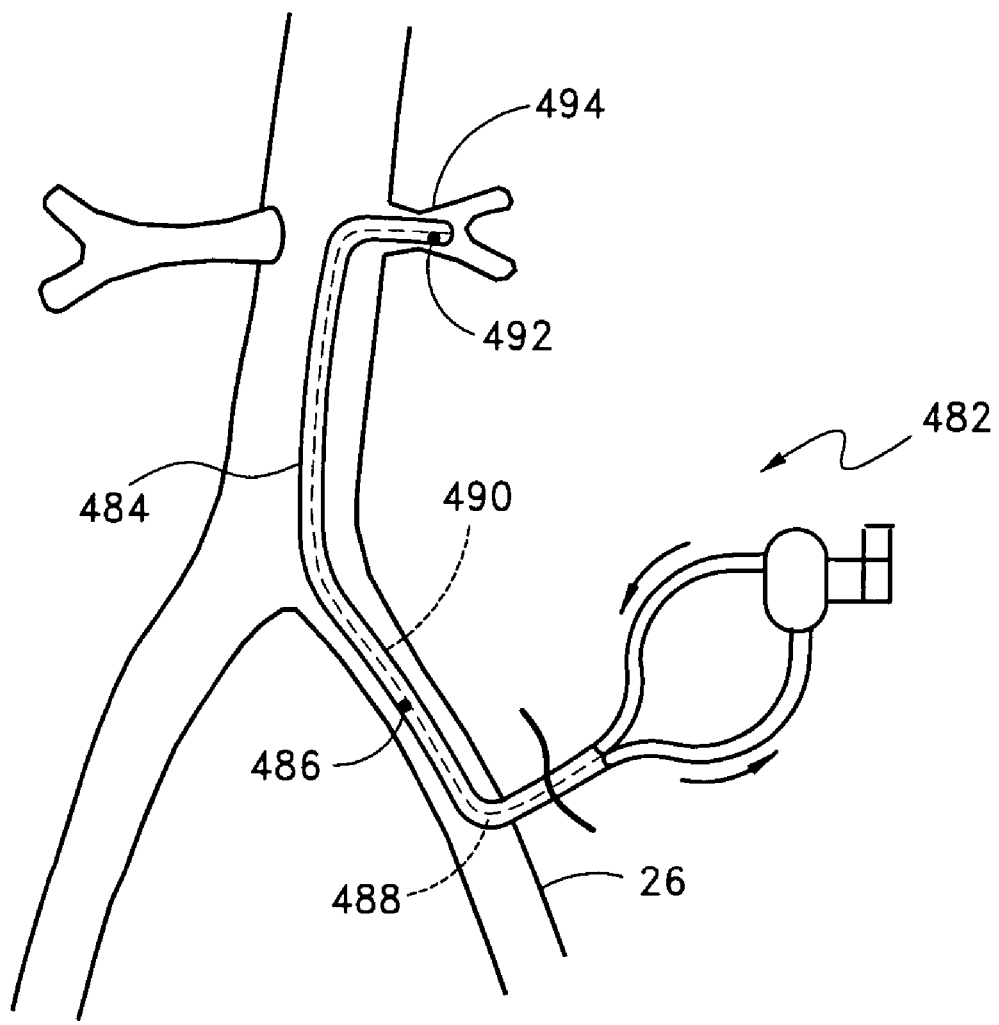
FIG. 11 is a schematic view of a modified embodiment of the heart assist system of FIG. 10, shown applied to a patient's vascular system.

FIGS. 10 and 11 illustrate extracardiac heart assist systems that employ an extravascular pump and that can be applied through as a single-site system. FIG. 10 shows a system 410 that is applied to a patient 12 through a single cannulation site 414 while inflow and outflow conduits fluidly communicate with non-primary vessels. The heart assist system 410 is applied to the patient 12 percutaneously through a single-site to couple two blood vessels with a pump 432. The pump 432 can have any of the features described in connection the pump 32. The pump 432 has an inflow conduit 450 and an outflow conduit 452 associated therewith. The inflow conduit 450 has a first end 456 and a second end 458. The first end 456 of the inflow conduit 450 is connected to the inlet of the pump 432 and the second end 458 of the inflow conduit 450 is fluidly coupled with a first non-primary blood vessel (e.g., the femoral artery 26) by way of a multilumen cannula 460. Similarly, the outflow conduit 452 has a first end 462 and a second end 464. The first end 462 of the outflow conduit 452 is connected to the outlet of the pump 432 and the second end 464 of the outflow conduit 452 is fluidly coupled with a second blood vessel (e.g., the descending aorta 16) by way of the multilumen cannula 460.

In one embodiment, the multilumen cannula 460 includes a first lumen 466 and a second lumen 468. The first lumen 466 extends from a proximal end 470 of the multilumen cannula 460 to a first distal end 472. The second lumen 468 extends from the proximal end 470 to a second distal end 474. In the illustrated embodiment, the second end 458 of the inflow conduit 450 is connected to the first lumen 466 of the multilumen cannula 460 and the second end 464 of the outflow conduit 452 is connected to the second lumen 468 of the multilumen cannula 460.

Where there is a desire for the patient 12 to be ambulatory, the multilumen cannula 460 preferably is made of material sufficiently flexible and resilient to permit the patient 12 to be comfortably move about while the multilumen cannula 460 is indwelling in the patient's blood vessels without causing any vascular trauma.

The application shown in FIG. 10 and described above results in flow from the first distal end 472 to the second distal end 474. Of course, the flow direction may be reversed using the same arrangement, resulting in flow from the distal end 474 to the distal end 472. In some applications, the system 410 is applied in an arterial-arterial fashion. For example, as illustrated, the multilumen cannula 460 can be inserted into the left femoral artery 26 of the patient 12 and guided superiorly through the descending aorta to one of numerous locations. In one application, the multilumen cannula 460 can be advanced until the distal end 474 is located in the aortic arch 476 of the patient 12. The blood could discharge, for example, directly into the descending aorta proximate an arterial branch, such as the left subclavian artery or directly into the peripheral mesenteric artery (not shown).

The pump 432 draws blood from the patient's vascular system in the area near the distal end 472 and into the lumen 466. This blood is further drawn into the lumen of the conduit 450 and into the pump 432. The pump 432 then expels the blood into the lumen of the outflow conduit 452, which carries the blood into the lumen 468 of the multilumen cannula 460 and back into the patient's vascular system in the area near the distal end 474.

FIG. 11 shows another embodiment of a heart assist system 482 that is similar to the heart assist system 410, except as set forth below. The system 482 employs a multilumen cannula 484. In one application, the multilumen cannula 484 is inserted into the left femoral artery 26 and guided superiorly through the descending aorta to one of numerous locations. Preferably, the multilumen cannula 484 has an inflow port 486 that is positioned in one application within the left femoral artery 26 when the cannula 484 is fully inserted so that blood drawn from the left femoral artery 26 is directed through the inflow port 486 into a first lumen 488 in the cannula 484. The inflow port 486 can also be positioned in any other suitable location within the vasculature, described herein or apparent to one skilled in the art. This blood is then pumped through a second lumen 490 in the cannula 484 and out through an outflow port 492 at the distal end of the cannula 484. The outflow port 492 may be situated within, for example, a mesenteric artery 494 such that blood flow results from the left femoral artery 26 to the mesenteric artery 494. The blood could discharge, for example, directly into the descending aorta proximate an arterial branch, such as the renal arteries, the left subclavian artery, or directly into the peripheral mesenteric artery 494, as illustrated in FIG. 11. Where there is a desire for the patient to be ambulatory, the multilumen cannula 484 preferably is made of material sufficiently flexible and resilient to permit the patient 12 to comfortably move about while the cannula 484 is indwelling in the patient's blood vessels without causing any vascular trauma.

As shown in FIG. 11, in some application and systems one or more conduits can be positioned between the cannula 460 and a pump or other source of liquid. In these applications and systems, any suitable structure or technique for coupling the cannula 460 and such a conduit can be used, including any of those described below in connection with FIGS. 17-23.

Further details of the multilumen cannula 460 may be found in U.S. patent application Ser. No. 10/078,283, filed Feb. 14, 2002, entitled A MULTILUMEN CATHETER FOR MINIMIZING LIMB ISCHEMIA. Also, any of the cannulae described herein can be altered to include any structure described in U.S. patent application Ser. No. 10/706,346, filed Nov. 12, 2003, entitled CANNULAE HAVING REDIRECTING TIP; U.S. application Ser. No. 11/083,042, filed Mar. 17, 2005; U.S. application Ser. No. 10/686,040, filed Oct. 15, 2003; U.S. application Ser. No. 11,057,692, filed Feb. 14, 2005; U.S. application Ser. No. 10/735,413, filed Dec. 12, 2003; and U.S. application Ser. No. 10/866,535, filed Jun. 10, 2004 which are hereby expressly incorporated by reference in its entirety and made a part of this specification.

Figure 12:
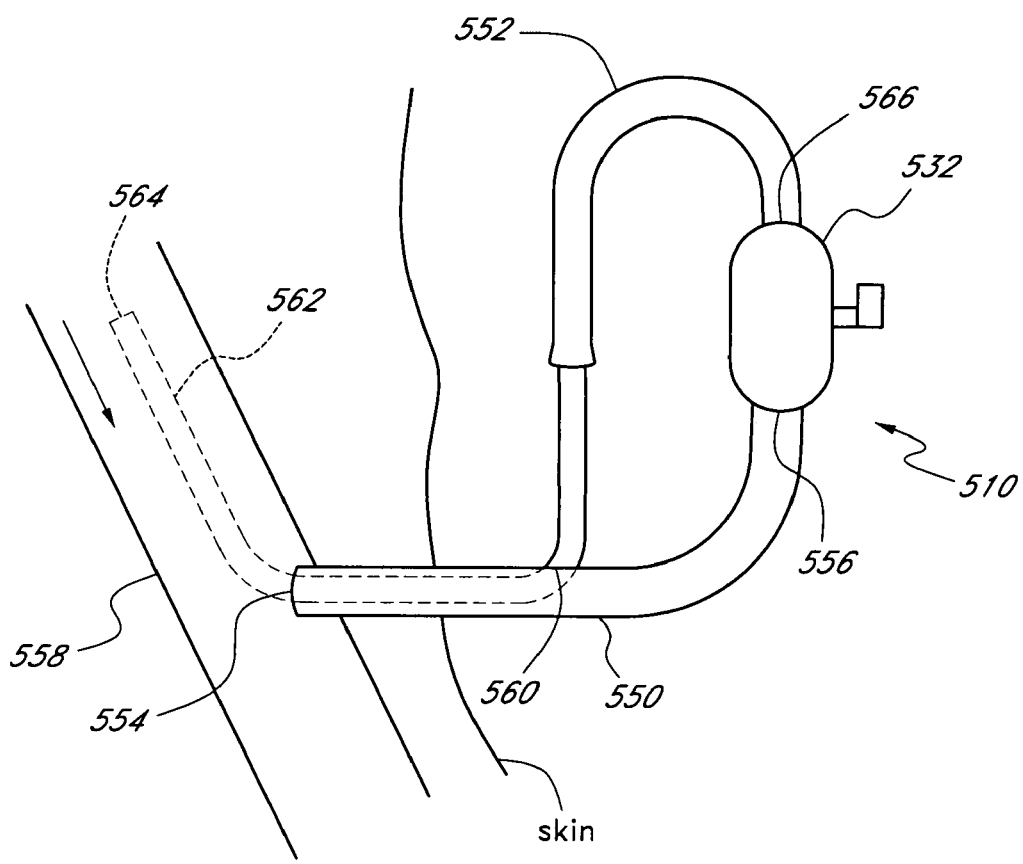
FIG. 12 is a schematic view of another embodiment of a heart assist system having multiple conduits for single-site application, shown applied to a patient's circulatory system.

FIG. 12 shows another heart assist system 510 that takes further advantage of the supplemental blood perfusion and heart load reduction benefits while remaining minimally invasive in application. The heart assist system 510 is an extracardiac pumping system that includes a pump 532, an inflow conduit 550 and an outflow conduit 552. In the illustrated embodiment, the inflow conduit 550 comprises a vascular graft. The vascular graft conduit 550 and the outflow conduit 552 are fluidly coupled to pump 532. The pump 532 is configured to pump blood through the patient at subcardiac volumetric rates, and has an average flow rate that, during normal operation thereof, is substantially below that of the patient's heart when healthy. In one variation, the pump 532 may be a rotary pump. Other pumps described herein, or any other suitable pump can also be used in the extracardiac pumping system 510. In one application, the pump 532 is configured so as to be implantable.

The vascular graft 550 has a first end 554 and a second end 556. The first end 554 is sized and configured to couple to a non-primary blood vessel 558 subcutaneously to permit application of the extracardiac pumping system 510 in a minimally-invasive procedure. In one application, the vascular graft conduit 550 is configured to couple to the blood vessel 558 via an anastomosis connection. The second end 556 of the vascular graft 550 is fluidly coupled to the pump 532 to conduct blood between the non-primary blood vessel 558 and the pump 532. In the embodiment shown, the second end 556 is directly connected to the pump 532, but, as discussed above in connection with other embodiments, intervening fluid conducting elements may be interposed between the second end 556 of the vascular graft 550 and the pump 532. Examples of arrangements of vascular graft conduits may be found in U.S. Pat. No. 6,761,700, issued Jul. 13, 2004, entitled EXTRA-CORPOREAL VASCULAR CONDUIT, which is hereby incorporated by reference in its entirety and made a part of this specification.

FIG. 12 illustrates that the present inventive embodiment further comprises means for coupling the outflow conduit 552 to the vascular graft 550, which may comprise in one embodiment an insertion site 560. In the illustrated embodiment, the insertion site 560 is located between the first end 554 and the second end 556 of the vascular graft 550. The outflow conduit 552 preferably is coupled with a cannula 562. The cannula 562 can take any suitable form and can be coupled with the conduit 552 by any suitable structure or technique, such as any of the techniques or structures discussed below in connection with FIGS. 17-23.

The insertion site 560 is configured to receive the cannula 562 therethrough in a sealable manner in the illustrated embodiment. In another embodiment, the insertion site 560 is configured to receive the outflow conduit 552 directly. The cannula 562 includes a first end 564 sized and configured to be inserted through the insertion site 560, through the cannula 550, and through the non-primary blood vessel 558. The conduit 552 has a second end 566 fluidly coupled to the pump 532 to conduct blood between the pump 532 and the blood vessel 558.

The extracardiac pumping system 510 can be applied to a patient, as shown in FIG. 12, so that the outflow conduit 552 provides fluid communication between the pump 532 and a location upstream or downstream of the location where the cannula 562 enters the non-primary blood vessel 558. In another application, the cannula 562 is directed through the blood vessel to a different blood vessel, upstream or downstream thereof. Although the vascular graft 550 is described above as an "inflow conduit" and the conduit 552 is described above as an "outflow conduit," in another application of this embodiment, the blood flow through the pumping system 510 is reversed (i.e., the pump 532 pumps blood in the opposite direction), whereby the vascular graft 550 is an outflow conduit and the conduit 552 is an inflow conduit.

Figure 13:
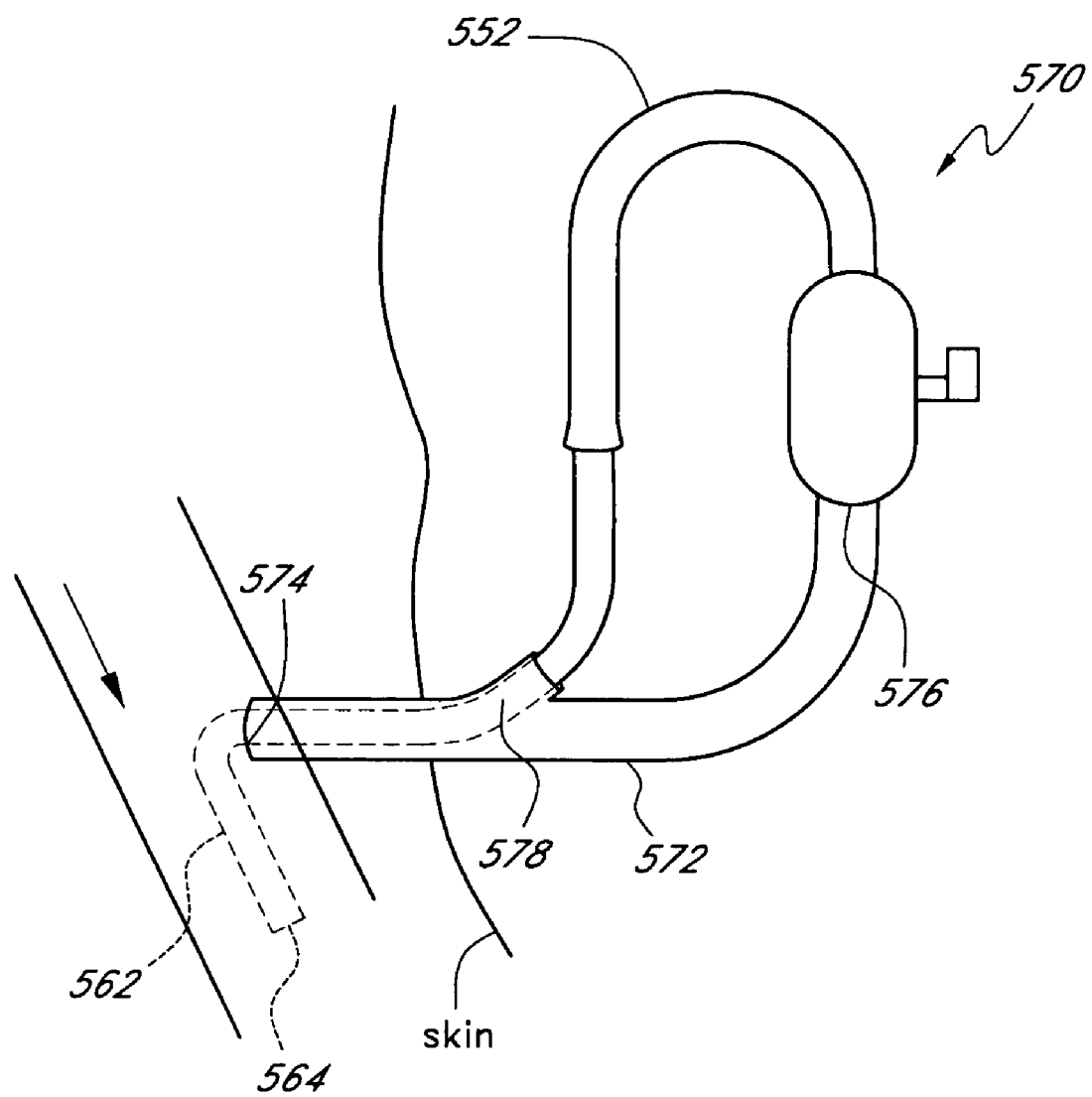
FIG. 13 is a schematic view of another application of the embodiment of FIG. 12, shown applied to a patient's vascular system.

FIG. 13 shows a variation of the extracardiac pumping system shown in FIG. 12. In particular, a heart assist system 570 includes an inflow conduit 572 that comprises a first end 574, a second end 576, and means for connecting the outflow conduit 552 to the inflow conduit 572. In one embodiment, the inflow conduit 572 comprises a vascular graft. The extracardiac pumping system 570 is otherwise similar to the extracardiac pumping system 510. The means for connecting the conduit 552 to the inflow conduit 572 may comprise a branched portion 578. In one embodiment, the branched portion 578 is located between the first end 574 and the second end 576. The branched portion 578 is configured to sealably receive the distal end 564 of the outflow conduit 552. Where, as shown, the first end 564 of the outflow conduit 552 comprises the cannula 562, the branched portion 578 is configured to receive the cannula 562. The inflow conduit 572 of this arrangement comprises in part a multilumen cannula, where the internal lumen extends into the blood vessel 558. Other multilumen catheter arrangements are shown in U.S. application Ser. No. 10/078,283, incorporated by reference herein above.

2. Single-Site Application of Intravascular Pumping Systems

Figure 14:
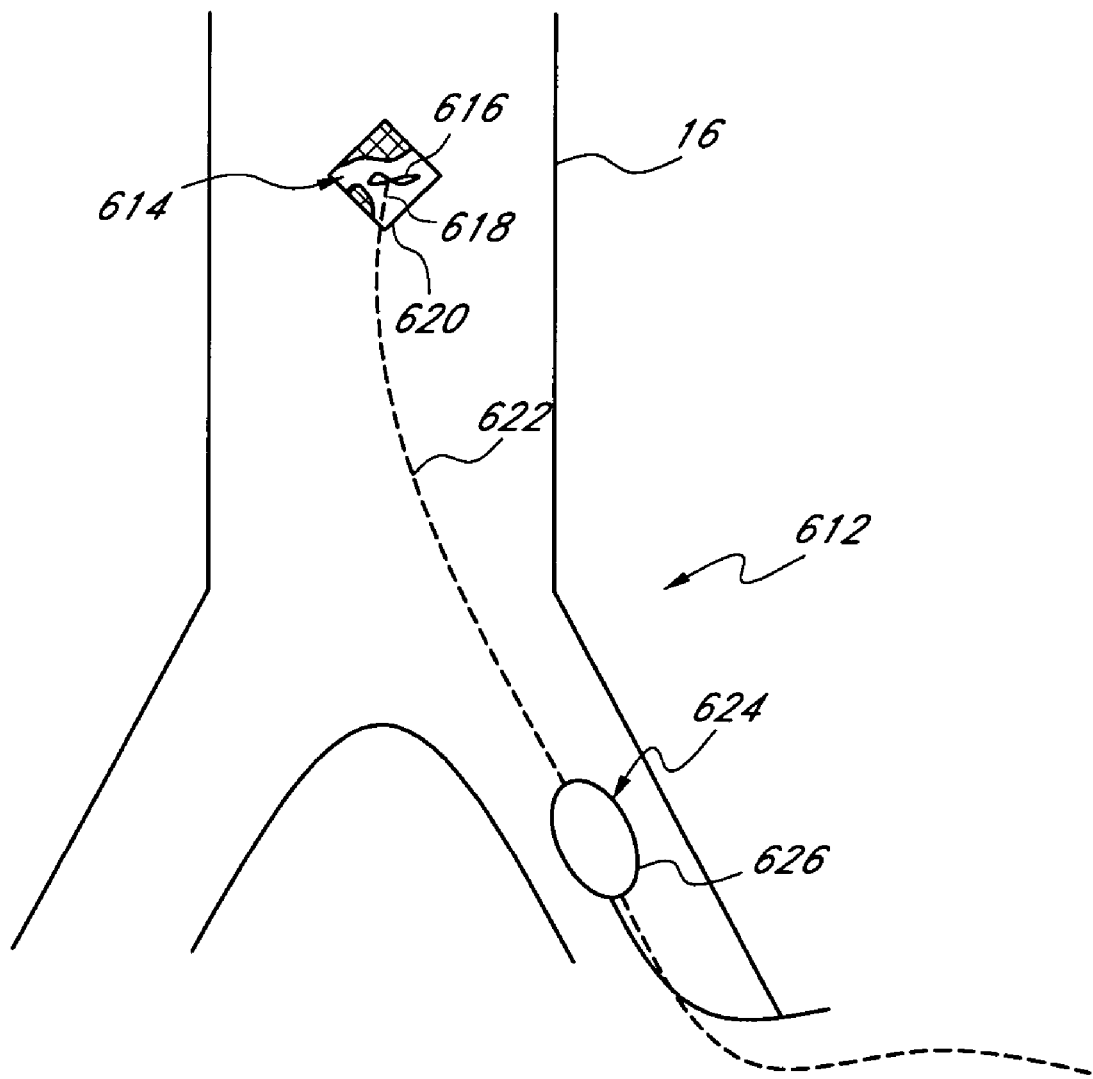
FIG. 14 is a schematic view of one application of an embodiment of a heart assist system having an intravascular pump enclosed in a protective housing, wherein the intravascular pump is inserted into the patient's vasculature through a non-primary vessel.
Figure 15:
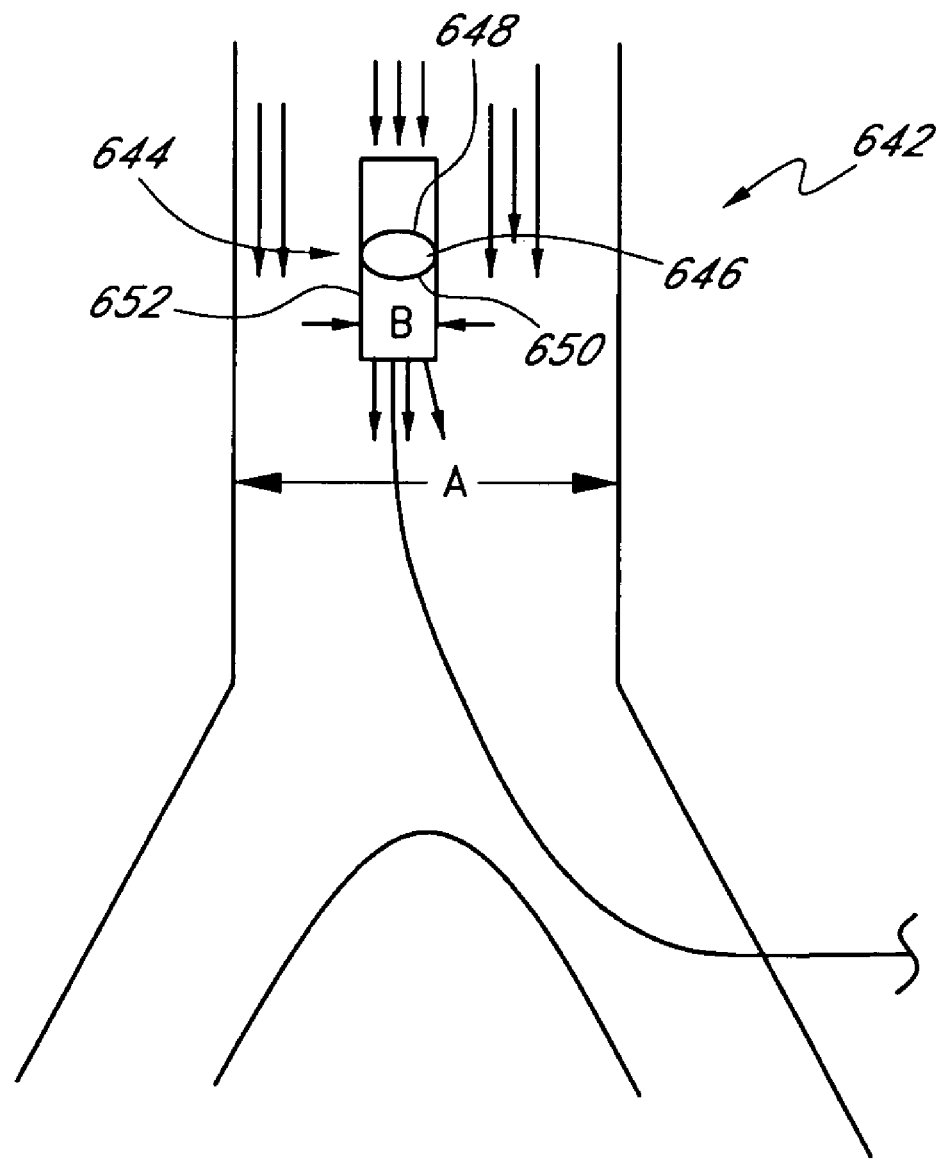
FIG. 15 is a schematic view of another embodiment of a heart assist system having an intravascular pump housed within a conduit having an inlet and an outlet, wherein the intravascular pump is inserted into the patient's vasculature through a non-primary vessel.

FIGS. 14-16 illustrate extracardiac heart assist systems that employ intravascular pumping systems. Such systems take further advantage of the supplemental blood perfusion and heart load reduction benefits discussed above while remaining minimally invasive in application. Specifically, it is contemplated to provide an extracardiac pumping system that comprises a pump that is sized and configured to be at least partially implanted intravascularly in any location desirable to achieve those benefits, while being insertable through a non-primary vessel.

FIG. 14 shows a heart assist system 612 that includes a pumping means 614 comprising preferably one or more rotatable impeller blades 616, although other types of pumping means 614 are contemplated, such as an archimedes screw, a worm pump, or other means by which blood may be directed axially along the pumping means from a location upstream of an inlet to the pumping means to a location downstream of an outlet from the pumping means. Where one or more impeller blades 616 are used, such as in a rotary pump, such impeller blades 616 may be supported helically or otherwise on a shaft 618 within a housing 620. The housing 620 may be open, as shown, in which the walls of the housing 620 are open to blood flow therethrough. The housing 620 may be entirely closed, if desired, except for an inlet and outlet (not shown) to permit blood flow therethrough in a more channel fashion. For example, the housing 620 could be coupled with or replaced by a cannula with a lumen that has an inner size that increases distally as discussed in U.S. patent application Ser. No. 10/866,535, filed Jun. 10, 2004, which is hereby incorporated by reference herein. The heart assist system 612 serves to supplement the kinetic energy of the blood flow through the blood vessel in which the pump is positioned, e.g., the aorta 16.

The impeller blade(s) 616 of the pumping means 614 of this embodiment may be driven in one or a number of ways known to persons of ordinary skill in the art. In the embodiment shown in FIG. 14, the impeller blade(s) 616 are driven mechanically via a rotatable cable or drive wire 622 by driving means 624, the latter of which may be positioned corporeally (intra- or extra-vascularly) or extracorporeally. As shown, the driving means 624 may comprise a motor 626 to which energy is supplied directly via an associated battery or an external power source, in a manner described in more detail herein. It is also contemplated that the impeller blade(s) 616 be driven electromagnetically through an internal or external electromagnetic drive. Preferably, a controller (not shown) is provided in association with this embodiment so that the pumping means 614 may be controlled to operate in a continuous and/or pulsatile fashion, as described herein.

Variations of the intravascular embodiment of FIG. 14 are shown in FIGS. 15 and 16. In the embodiment of FIG. 15, an intrasvascular extracardiac system 642 comprising a pumping means 644, which may be one of several means described herein. The pumping means 644 may be driven in any suitable manner, including means sized and configured to be implantable and, if desired, implantable intravascularly, e.g., as discussed above. For a blood vessel (e.g., descending aorta) having a diameter "A", the pumping means 644 preferably has a meaningfully smaller diameter "B". The pumping means 644 may comprise a pump 646 having an inlet 648 and an outlet 650. The pumping means 644 also comprises a pump driven mechanically by a suitable drive arrangement in one embodiment. Although the vertical arrows in FIG. 15 illustrate that the pumping means 644 pumps blood in the same direction as the flow of blood in the vessel, the pumping means 644 could be reversed to pump blood in a direction generally opposite of the flow in the vessel.

In one embodiment, the pumping means 644 also includes a conduit 652 in which the pump 646 is housed. The conduit 652 may be relatively short, as shown, or may extend well within the designated blood vessel or even into an adjoining or remote blood vessel at either the inlet end, the outlet end, or both. The intravascular extracardiac system 642 may further comprise an additional parallel-flow conduit, as discussed below in connection with the system of FIG. 16.

The intrasvascular extracardiac system 642 may further comprise inflow and/or outflow conduits or cannulae (not shown) fluidly connected to the pumping means 644, e.g., to the inlet and outlet of pump 646. Any suitable conduit or cannula can be employed. For example, a cannula defining a lumen with an inner size that increases distally, as discussed herein or in the applications incorporated by reference herein could be coupled with an intravascular extracardiac system.

In another embodiment, an intrasvascular pumping means 644 may be positioned within one lumen of a multilumen catheter so that, for example, where the catheter is applied at the left femoral artery, a first lumen may extend into the aorta proximate the left subclavian and the pumping means may reside at any point within the first lumen, and the second lumen may extend much shorter just into the left femoral or left iliac. Such a system is described in greater detail in U.S. application Ser. No. 10/078,283, incorporated by reference herein above.

FIG. 16 shows a variation of the heart assist system of FIG. 15. In particular the intravascular system may further comprise an additional conduit 660 positioned preferably proximate the pumping means 644 to provide a defined flow path for blood flow axially parallel to the blood flowing through the pumping means 644. In the case of the pumping means 644 of FIG. 16, the means comprises a rotatable cable 662 having blood directing means 664 supported therein for directing blood axially along the cable. Other types of pumping means are also contemplated, if desired, for use with the additional conduit 660.

The intravascular extracardiac system described herein may be inserted into a patient's vasculature in any means known by one of ordinary skill or obvious variant thereof. In one method of use, such a system is temporarily housed within a catheter that is inserted percutaneously, or by surgical cutdown, into a non-primary blood vessel and advanced through to a desired location. The catheter preferably is then withdrawn away from the system so as not to interfere with operation of the system, but still permit the withdrawal of the system from the patient when desired. Further details of intravascular pumping systems may be found in U.S. patent application Ser. No. 10/686,040, filed Oct. 15, 2003, which is hereby incorporated by reference herein in its entirety.

C. Potential Enhancement of Systemic Arterial Blood Mixing

One of the advantages of the present invention is its potential to enhance mixing of systemic arterial blood, particularly in the aorta. Such enhanced mixing ensures the delivery of blood with higher oxygen-carrying capacity to organs supplied by arterial side branches off of the aorta. A method of enhancing mixing utilizing the present invention preferably includes taking steps to assess certain parameters of the patient and then to determine the minimum output of the pump that, when combined with the heart output, ensures turbulent flow in the aorta, thereby enhancing blood mixing.

Blood flow in the aortic arch during normal cardiac output may be characterized as turbulent in the end systolic phase. It is known that turbulence in a flow of fluid through pipes and vessels enhances the uniform distribution of particles within the fluid. It is believed that turbulence in the descending aorta enhances the homogeneity of blood cell distribution in the aorta. It is also known that laminar flow of viscous fluids leads to a higher concentration of particulate in the central portion of pipes and vessels through which the fluid flows. It is believed that, in low flow states such as that experienced during heart failure, there is reduced or inadequate mixing of blood cells leading to a lower concentration of nutrients at the branches of the aorta to peripheral organs and tissues. As a result, the blood flowing into branch arteries off of the aorta will likely have a lower hematocrit, especially that flowing into the renal arteries, the celiac trunk, the spinal arteries, and the superior and inferior mesenteric arteries. That is because these branches draw from the periphery of the aorta The net effect of this phenomenon is that the blood flowing into these branch arteries has a lower oxygen-carrying capacity, because oxygen-carrying capacity is directly proportional to both hematocrit and the fractional $O_2$ saturation of hemoglobin. Under those circumstances, it is very possible that these organs will experience ischemia-related pathology.

The phenomenon of blood streaming in the aorta, and the resultant inadequate mixing of blood resulting in central lumenal concentration of blood cells, is believed to occur when the Reynolds number ($N_R$) for the blood flow in the aorta is below 2300. To help ensure that adequate mixing of blood will occur in the aorta to prevent blood cells from concentrating in the center of the lumen, a method of applying the present invention to a patient may also include steps to adjust the output of the pump to attain turbulent flow within the descending aorta upstream of the organ branches; i.e., flow exhibiting a peak Reynolds number of at least 2300 within a complete cycle of systole and diastole. Because flow through a patient is pulsatile in nature, and not continuous, consideration must be given to how frequently the blood flow through the aorta has reached a certain desired velocity and, thus, a desired Reynolds number. The method contemplated herein, therefore, should also include the step of calculating the average Womersley number ($N_W$), which is a function of the frequency of the patient's heart beat. It is desired that a peak Reynolds number of at least 2300 is attained when the corresponding Womersley number for the same blood flow is approximately 6 or above.

More specifically, the method may comprise calculating the Reynolds number for the blood flow in the descending aorta by determining the blood vessel diameter and both the velocity and viscosity of the fluid flowing through the aorta. The Reynolds number may be calculated pursuant to the following equation:

$$N_R = \frac{V \cdot d}{\upsilon}$$

where: V=the velocity of the fluid; d=the diameter of the vessel; and v=the viscosity of the fluid. The velocity of the blood flowing through the aorta is a function of the cross-sectional area of the aorta and the volume of flow therethrough, the latter of which is contributed both by the patient's own cardiac output and by the output of the pump of the present invention. Velocity may be calculated by the following equation:

$$V = \frac{Q}{\pi r^2}$$

where Q=the volume of blood flowing through the blood vessel per unit time, e.g., the aorta, and r=radius of the aorta. If the relationship between the pump output and the velocity is already known or independently determinable, the volume of blood flow Q may consist only of the patient's cardiac output, with the knowledge that that output will be supplemented by the subcardiac pump that is part of the present invention. If desired, however, the present system can be implemented and applied to the patient first, before calculating Q, which would consist of the combination of cardiac output and the pump output.

The Womersley number may be calculated as follows:

$$N_W = r\sqrt{2\pi\omega/\upsilon}$$

where r is the radius of the vessel being assessed, ω is the frequency of the patient's heartbeat, and v=the viscosity of the fluid. For a peak Reynolds number of at least 2300, a Womersley number of at least 6 is preferred, although a value as low as 5 would be acceptable.

By determining (i) the viscosity of the patient's blood, which is normally about 3.0 mm$^2$/sec (kinematic viscosity), (ii) the cardiac output of the patient, which of course varies depending upon the level of CHF and activity, and (iii) the diameter of the patient's descending aorta, which varies from patient to patient but is about 21 mm for an average adult, one can determine the flow rate Q that would result in a velocity through the aorta necessary to attain a Reynolds number of at least 2300 at its peak during the patient's heart cycle. Based upon that determination of Q, one may adjust the output of the pump of the present invention to attain the desired turbulent flow characteristic through the aorta, enhancing mixing of the blood therethrough.

One may use ultrasound (e.g., echocardiography or abdominal ultrasound) to measure the diameter of the aorta, which is relatively uniform in diameter from its root to the abdominal portion of the descending aorta. Furthermore, one may measure cardiac output using a thermodilution catheter or other techniques known to those of skill in the art. Finally, one may measure viscosity of the patient's blood by using known methods; for example, using a capillary viscosimeter. It is expected that in many cases, the application of this embodiment of the present method will provide a basis to more finely tune the system to more optimally operate the system to the patient's benefit. Other methods contemplated by the present invention may include steps to assess other patient parameters that enable a person of ordinary skill in the art to optimize the present system to ensure adequate mixing within the vascular system of the patient.

Alternative inventive methods that provide the benefits discussed herein include the steps of, prior to applying a shape change therapy, applying a blood supplementation system (such as one of the many examples described herein) to a patient, whereby the methods are designed to improve the ability to reduce the size and/or wall stress of the left ventricle, or both ventricles, thus reducing ventricular loading. Specifically, one example of such a method comprises the steps of providing a pump configured to pump blood at subcardiac rates, providing inflow and outflow conduits configured to fluidly communicate with non-primary blood vessels, fluidly coupling the inflow conduit to a non-primary blood vessel, fluidly coupling the outflow conduit to the same or different (primary or non-primary) blood vessel and operating the subcardiac pump in a manner, as described herein, to reduce the load on the heart, wherein the fluidly coupling steps may comprise anastomosis, percutaneous cannulazation, positioning the distal end of one or both conduits within the desired terminal blood vessel or any combination thereof. The method further comprises, after sufficient reduction in ventricular loading, applying a shape change therapy in the form of, for example, a cardiac reshaping device, such as those referred to herein, or others serving the same or similar function, for the purpose of further reducing the size of and/or wall stress on one or more ventricles and, thus, the heart, and/or for the purpose of maintaining the patient's heart at a size sufficient to enhance recovery of the patient's heart.

II. Systems and Techniques for Priming a Fluid Circuit

As discussed above, a variety of systems can be applied to a patient to provide an efficacious treatment, such as one offloading the heart in connection with congestive heart failure. It is generally preferred that such systems are coupled with a patient in a manner that minimizes or completely prevents the introduction of embolic matter, e.g., particles or gases, into the blood stream. It would be advantageous to provide structures and techniques for such a coupling or connection, which techniques and structures are sometimes referred to herein as "priming."

FIGS. 17-23 illustrate a variety of structures useful for priming fluid circuits. As discussed further below, such structures can be deployed for medical treatments that involve circulating blood, components of blood, or other bodily fluids, and these structures also are useful for providing a fluid flow circuit connection with little or no foreign matter outside medical contexts.

Figure 17:
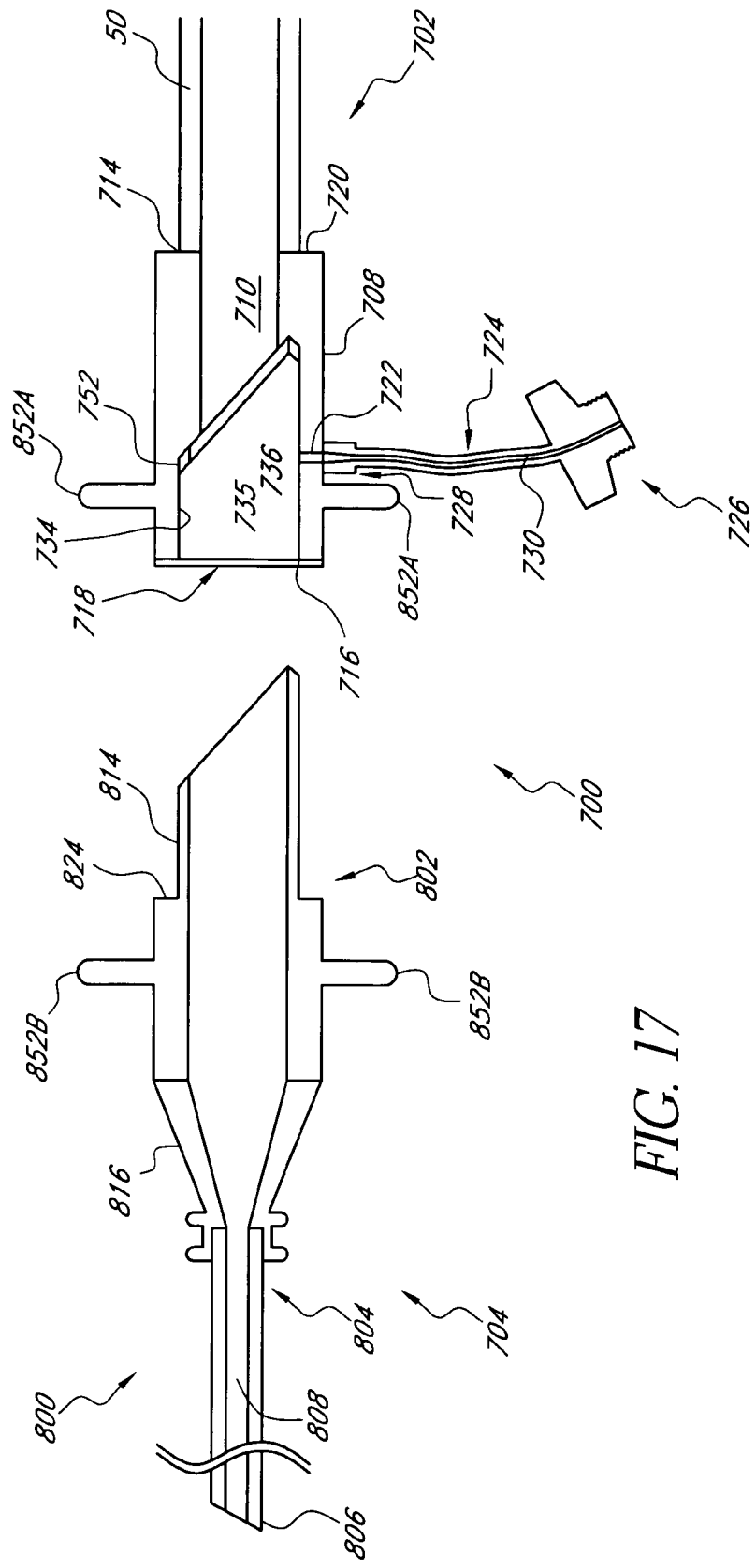
FIG. 17 is a cross-sectional view of one embodiment of a system for priming a liquid circuit.

FIG. 17 shows one embodiment of a system 700 for priming a liquid circuit. As discussed further below, the system 700 can be applied to any liquid circuit, including circuits designed to convey biological fluid, e.g., whole blood or any subset thereof, such as plasma. The system 700 initially is discussed in connection with some components of the heart assist system 10 but also is applicable to the other heart assist systems described herein and other systems that may be similar. However, the system 700 can be used in connection with any of the systems disclosed herein and with other fluid circuits as discussed below. FIG. 17 illustrates that in one embodiment, the system 700 includes a tube assembly 702 and a cannula assembly 704.

The tube assembly 702 includes a tube and a tube connector 706. In the illustrated embodiment, the tube comprises the outflow conduit 50, which can be coupled with the pump 36, of the system 10 as illustrated in FIG. 1. The tube connector 706 includes a housing 708 in one embodiment that can be made of a suitable material such as a polycarbonate, PVC, acrylic, polystyrene, or another similar material. A lumen 710 can be formed in the housing 708 and can be provided with a first housing cross-sectional area 712. In some embodiments, the housing 708 has or is coupled with (e.g., fluidly coupled with) one or multiple lumens. Preferably the lumen 710 is a main lumen where the housing 708 has a plurality of lumens. As used herein, the term "main lumen" is a broad term that includes configurations where the lumen 710 is the largest lumen formed in or connected to the largest lumen in the housing 708. The term "main lumen" also includes a lumen that is the primary lumen used to conduct fluid during the majority of the use of the conduit 50, e.g., a lumen not closed off during operation of the system 10.

The tube connector 706 and the outflow conduit 50 can be coupled in any suitable manner. For example, an adhesive can be used to join these components together. In the illustrated embodiment, a junction 714 is provided between the outflow conduit 50 and the housing 708. The junction 714 can be a butt-end junction, as shown. In another embodiment, at least a portion of the second end 58 of the conduit 50 is inserted into the housing 708. Where the second end 58 of the conduit 50 is inserted into the housing 708, one end of the housing preferably includes an enlarged lumen and the opposite end of the housing 708 includes a smaller lumen. Preferably, the enlarged lumen of the housing 708 is large enough to receive the second end 58 of the conduit 50, such that a seamless blood flow path is provided between the smaller lumen end of the housing 708 and the lumen of the conduit 50. Any suitable technique can be used for connecting the conduit 50 to the housing 708 where the housing is configured to have a portion of the conduit inserted thereinto. For example, an adhesive can be used to secure the second end 58 of the conduit 50 within the housing 708. At least one of the tube assembly 702 and the cannula assembly 704 and other similar structures can be made as single unitary structures that are not assembled by a practitioner.

The housing 708 also comprises a first port 716 and a membrane 718 that extends across the first port 716. The membrane 718 can be coupled with the housing 708 in any suitable manner. For example, the membrane 718 can be secured to the first port 716 by an adhesive or integrally formed therewith. In other embodiments discussed below, a screw cap is used to secure the membrane 718 to the housing 708. As discussed further below, a screw cap and a gasket or other suitable seal can be provided to substantially reduce or completely prevent fluid from inadvertently leaking out of the tube connector 706.

In one embodiment, the membrane 718 is permeable to gas. The gas permeable embodiments of the membrane 718 are advantageous for one primary technique wherein a liquid is forced into the housing 708 and the liquid thereafter flows toward the membrane 718. As the liquid flows toward the membrane 718, any gas found in the housing will be forced out of the housing through the membrane. The membrane 718 could also be configured to permit at least one component of the liquid to flow therethrough, while preventing other components of the liquid from flowing therethrough. In this sense, the membrane 718 can also perform a filtering function. The membrane 718 can be formed of a high density fiber material in some arrangements, e.g., polyethylene.

In one embodiment, the housing 708 includes a second port 720 that is configured to couple with the outflow conduit 50 or of another tube. As discussed above, at least a portion of the second end 58 can be coupled with the housing 708 or inserted into the housing, e.g., through the second port 720.

Figure 20:
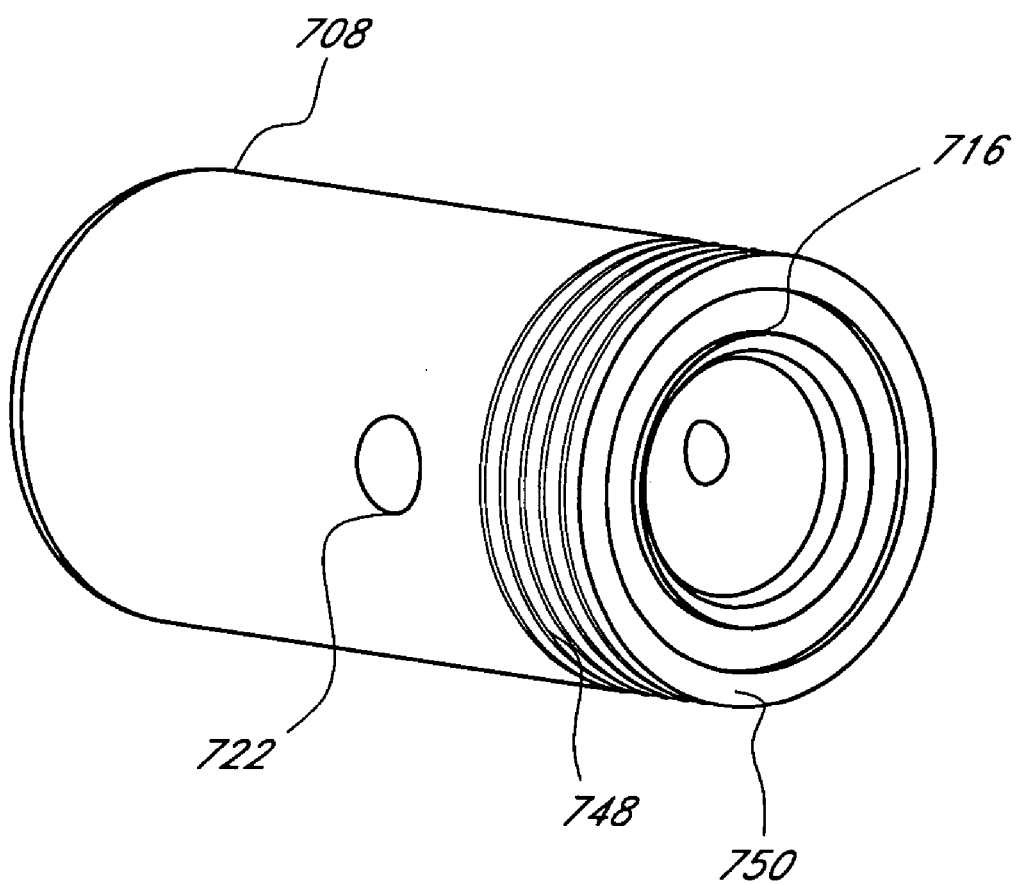
FIG. 20 is a perspective view of a housing for a pump tube connector, which can form a part of the connector system of FIG. 18.
Figure 21:
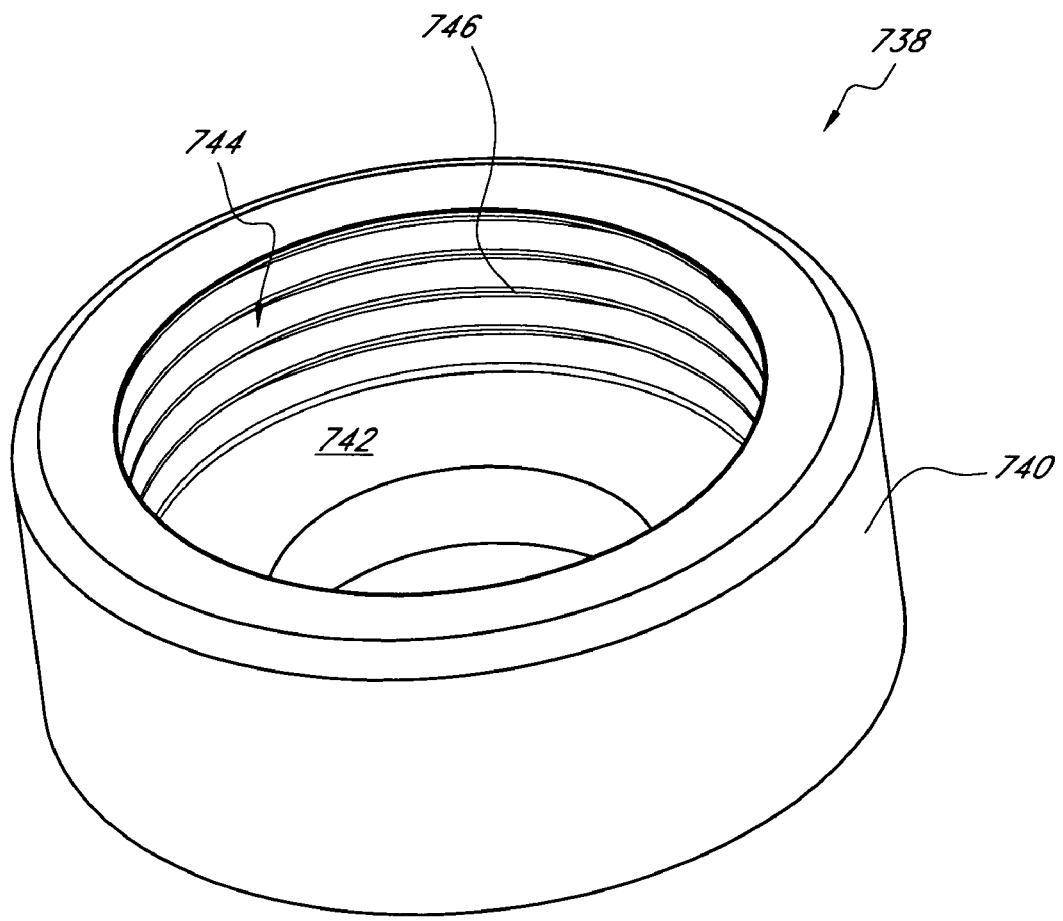
FIG. 21 is a perspective view of a removable cap configured to be mounted to the housing of FIG. 20.
Figure 22:
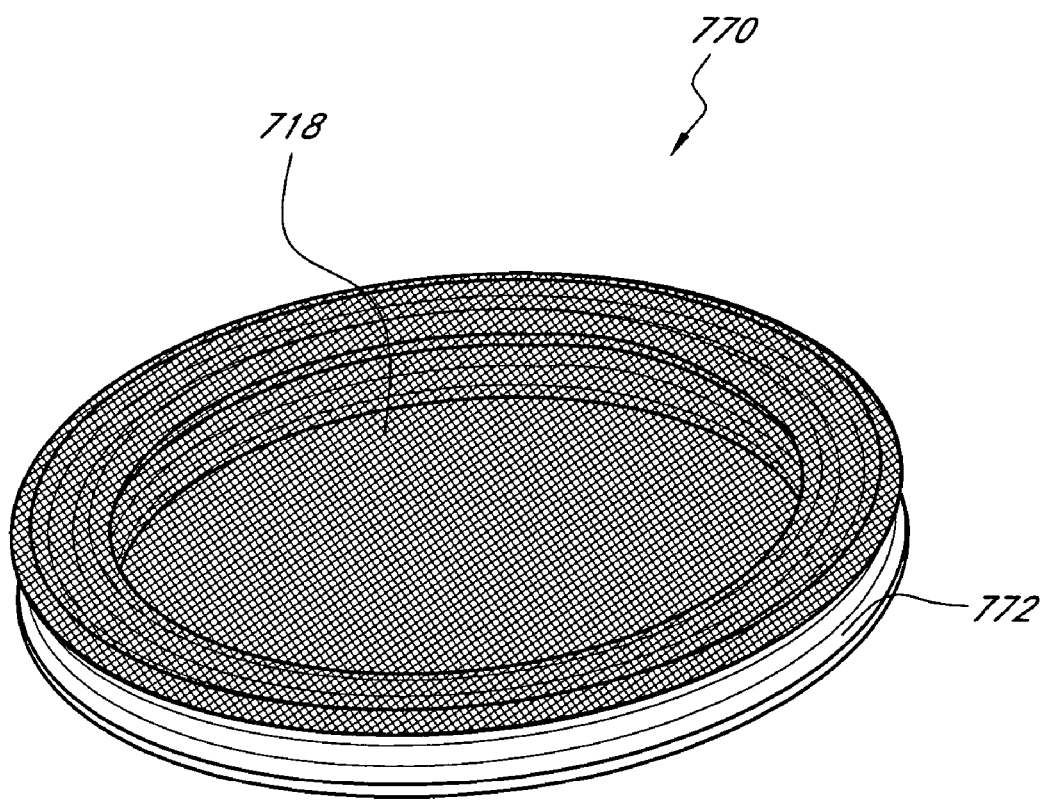
FIG. 22 is a perspective view of a membrane assembly including a membrane configured to be positioned between the cap of FIG. 21 and the housing of FIG. 20.

In one embodiment, the housing 708 also includes a third port 722. In some applications, the third port 722 is configured to couple with a source of liquid. For example, a tube 724 that can be configured to convey a suitable liquid can be coupled with the third port 722. Where used, the tube 724 includes a first end 726, a second end 728, and a lumen 730 extending therebetween. The lumen 730 is sometimes referred to herein as a "secondary" lumen. In some arrangements, the housing 708 includes a plurality of side ports that each can be configured as a third port 722, as shown in FIG. 20.

In one technique for priming a system, the first end 726 is coupled with a source of liquid and the second end 728 is in fluid communication with the lumen 710. As discussed above and further below, liquid can be forced from the first end 726 to the second end 728 through the lumen 730 and into the lumen 710. In some techniques, the fluid can further be forced out of the first port 716 through the membrane 718. Where the system 700 is used in a biological system, e.g., in connection with the system 10 or the other systems described herein, or other cardiovascular treatments, the first end 726 preferably is coupled with a source of bio-compatible liquid, such as saline.

In some embodiments, it is advantageous to provide a seamless, or smooth lumen throughout the fluid circuit. For example, in connection with circulating blood, seamless lumens can minimize damage to blood cells that can occur when blood cells are forced to flow along a path that is not seamless or smooth, e.g., a discontinuous flow path. In one arrangement, the system 700 comprises an arrangement that minimizes or eliminates discontinuities therein. One arrangement for minimizing or eliminating discontinuities provides an internal surface 732 formed inside the housing 708. The internal surface 732 preferably is a circumferential surfaces that extends inwardly from an inner wall 734 of the housing 708 toward a longitudinal axis of the lumen 710.

As discussed further below, the surface 732 can be configured to engage an end surface of the cannula assembly 704, whereby discontinuities in a blood flow path or other artifacts preventing seamless or smooth blood flow over the surface 732 can be eliminated or reduced to a clinically insignificant level. In one embodiment, the internal surface 732 is angled relative to the longitudinal axis of the lumen 710 such that the surface 732 has a distal region 735 and a proximal region 736.

In one embodiment, at least the region of the housing 708 that includes the surface 732 is configured to provide a seal along the point of connection between the tube assembly 702 and the cannula assembly 704. One technique for providing a seal involves configuring the surface 732 to accommodate at least a portion of the cannula assembly 704, e.g., to be deform when the cannula assembly 704 is urged into contact with the surface 732. Such deformation or accommodation can eliminate or minimize voids between these structures. In one embodiment, the surface 732 comprises a soft material that enhances sealing along the surface 732 and that accommodates at least a portion of the cannula assembly 704. Silicone is one material that is soft enough to deform to prevent such voids.

In one embodiment, the tube assembly 702 is configured such that the membrane 718 is not permanently fixed to the housing 708. This arrangement enables replacement of the membrane 718, or reuse of at least a portion of the tube assembly 702 where the system 700 is not configured as a disposable system. For example, in many non-medical applications, the conditions under which a system similar to the system 700 may require expensive materials or construction techniques. In such cases, the cost of the components of the system will increase. Also, in some non-medical applications there may be little or no risk of contamination associated with the reuse of a liquid priming system. In these and other similar contexts, reuse of the priming system is contemplated. In many medical applications, the components of the system 700 can be disposable, e.g., made of low-cost materials such as plastic. Disposable systems provide more assurance that the system will be sterile and will not introduce bacteria or contaminants into the bloodstream of the patient.

In one embodiment, the tube assembly 702 includes a removable cap 738. The removable end cap 738 can be coupled with the housing 708 adjacent to the first port 716. In one embodiment, the end cap 738 includes an engagement portion 740 that extends along the longitudinal axis of the lumen 710 when the cap 738 is coupled with the housing 708 and an end portion 742 that extends transversely engagement portion. The cap 738 is configured to engage the housing 708 adjacent to the first port 716. For example, in one embodiment a recess 744 is defined within the end cap 738. The recess 744 can be defined between the engagement portion 740 and the end portion 742. In one embodiment, the recess 744 is larger than the outer size of the housing 708. In one embodiment, the engagement portion 740 includes internal threads 746 that extend between the end portion 742 and an end of the engagement portion 740 opposite the end portion. The threads 746 are configured to mate with corresponding external threads 748 formed on the housing 708 adjacent to the first port 716. The threads 746, 748 enable the end cap 738 to be advanced onto the housing 708 and secured thereon.

In one technique, the membrane 718 is configured to be positioned between the housing 708 and the end cap 738 and to be secured therein by advancing the end cap 738 onto the housing 708 using the threads 746, 748. For example, the membrane 718 can be positioned between the end portion 742 and an end surface 750 of the housing 708 adjacent to the first port 716.

In one arrangement, the membrane 718 comprises a portion of a membrane assembly 770 that is configured to be secured between the end cap 738 and the housing 708. The membrane assembly 770 preferably is configured to be securely positioned within the tube assembly 702. In one arrangement, the membrane assembly 770 includes a seal member 772 configured to be positioned between the surfaces 742, 750. The seal member 772 can be an O-ring or other similar compressible member. In one arrangement, the membrane 718 is attached to the seal member 772, e.g., by a suitable adhesive.

The cannula assembly 704 comprises a cannula 800, which may be similar to the inflow cannula 60 shown in FIG. 1, and a cannula connector 802. The cannula 800 includes a first end 804 and a second end 806 configured to couple with a source of liquid to be conveyed in the circuit. As discussed further below, the first end 804 is coupled with the cannula connector 802 in a suitable fashion. The second end 806 is shown as a straight, angled member. As discussed in U.S. application Ser. No. 10/706,346, filed Nov. 12, 2003, which is hereby incorporated by reference herein, the second end 806 can take a variety of shapes and configurations that advantageously direct blood being delivered into or removed from the vasculature. The system 700 can be used in connection with any of these cannula designs. The cannula 800 defines a portion of a cannula lumen 808 that has a first cross-sectional area. The first cross-sectional area is located generally distally of the cannula connector 802 and can be generally constant along the length of the lumen 808 or can vary along this length, e.g., increasing in size toward the second end 806. A variety of configurations for the cannula 800 and tips therefore are described in U.S. application Ser. No. 10/866,535, filed Jun. 10, 2004.

The cannula connector 802 includes a piercing member 814. In some arrangement, a portion of the blood flow path through the cannula assembly 704 is located in the cannula connector 802, e.g., within the piercing member 814. In one embodiment, the cannula lumen 800 has a second cross-section or cross-sectional area adjacent or within the piercing member 814. In one embodiment, the second cross-sectional area is substantially the same as the first cross-sectional area. This arrangement provides a seamless lumen, which encourages smooth blood flow between the lumen 808 in the cannula 800 and the cannula connector 802. Smooth flow reduces or eliminates perturbations in the flow that could create biological reactions within the blood, such as thrombosis. In one arrangement, the flow is substantially laminar from within the cannula 800 to within the cannula connector 802. As discussed above, the terms "seamless" and "seamless lumen" are broad terms describing a blood flow path or a portion of a blood flow path that is configured to promote a smooth flow, a laminar flow, or any other fluid flow regime that prevents or minimizes damage to a delicate fluid. Seamless lumens can be provided in unitary extrusions or in assemblies that when assembled do not present significant steps in the flow patch. For example, an assembly of two structures that have lumen segments that can be joined at mating edges are seamless if they present a step of less than a percentage of the size of the lumen, for example less than about 10 percent. A lesser step as a percentage of size would perform even better in some arrangements, e.g., less than about 5 percent. A even smaller step as a percentage of size would perform even better in some arrangements, e.g., less than about 2 percent. In one arrangement, a blood flow lumen is provided that has an inner diameter of about 0.25 inches and the size of a step can be maintained to less than about 0.005 inches (about 0.13 mm).

In the embodiment of FIG. 17, the cannula connector 802 has a second cross-sectional area within the piercing member 814 that is larger than the cross-sectional area within the cannula 800. The cross-sectional area change can be provided by a transition section 816 located between the piercing member 814 and the cannula 800. The transition section 816 has varying cross-sectional area along its length in one embodiment. The variation in cross-sectional area can be generally constant, or linear, or can vary in any other suitable fashion to transition the blood from flowing in the within the cannula 800 to flowing within the cannula connector 802. By increasing the size of the lumen 808 defined within the cannula assembly 704, the transition from the cannula assembly 704 to the lumen 710 can be seamless, reducing the chance of thrombosis or other negative flow-perturbation-induced reaction in the blood, biologic, or other delicate fluid.

Figure 18:
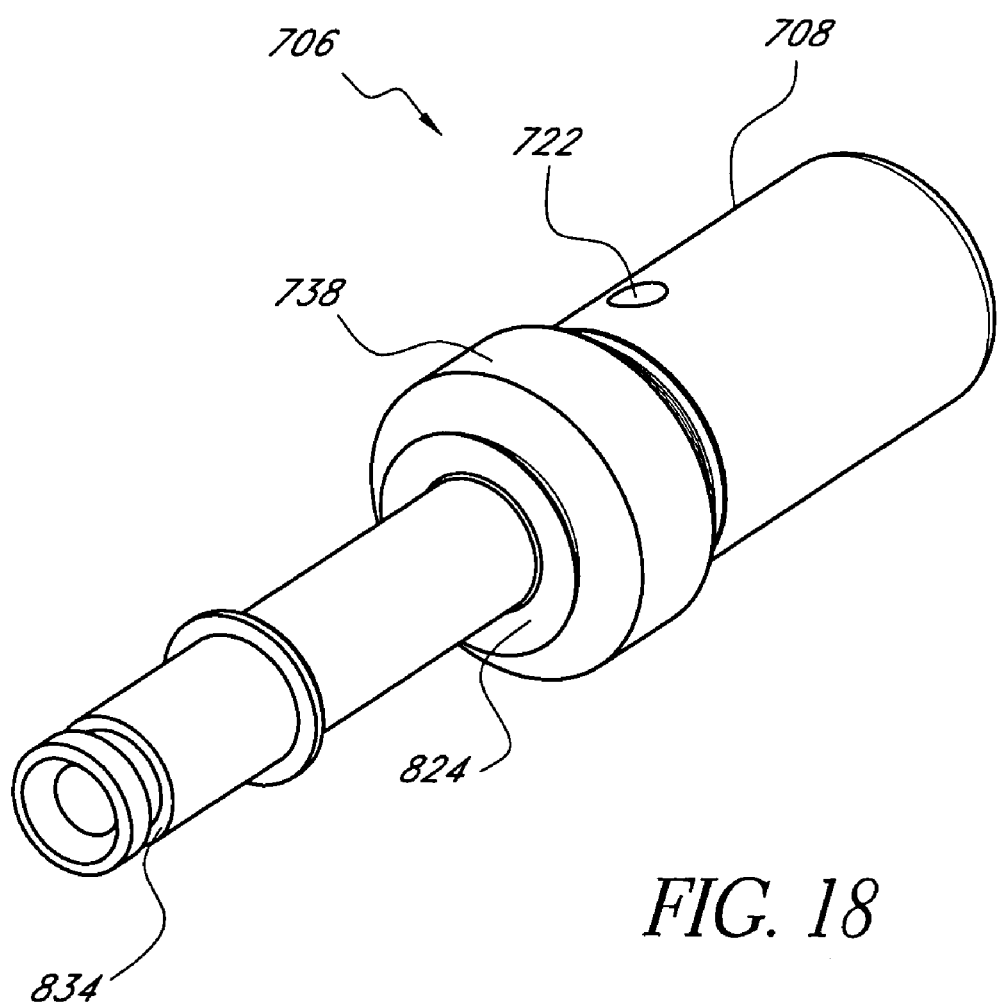
FIG. 18 is a perspective view of a connector system for use in primary a liquid circuit, such as that of FIG. 17.
Figure 19:
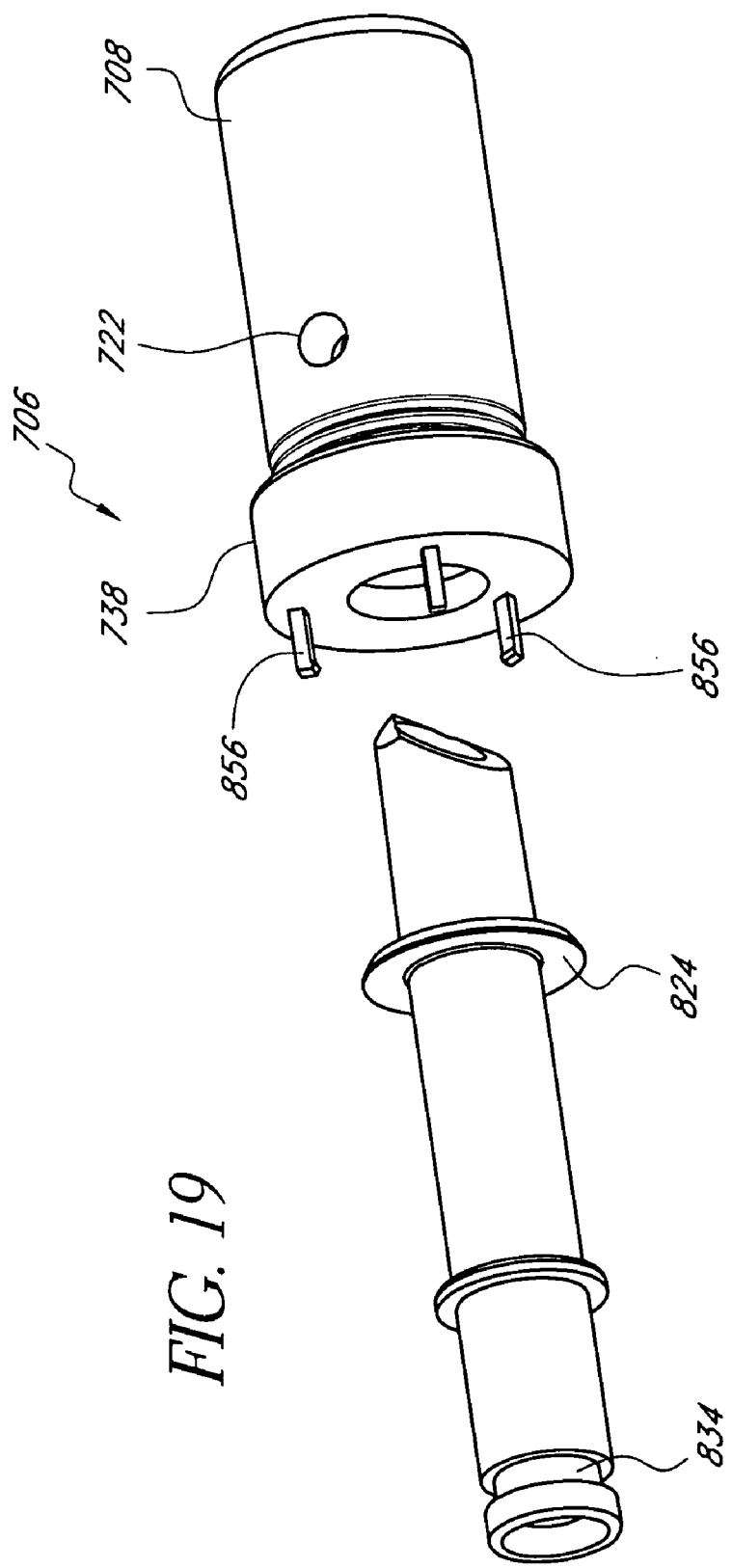
FIG. 19 is an exploded perspective view of the connector system of FIG. 18.
Figure 23:
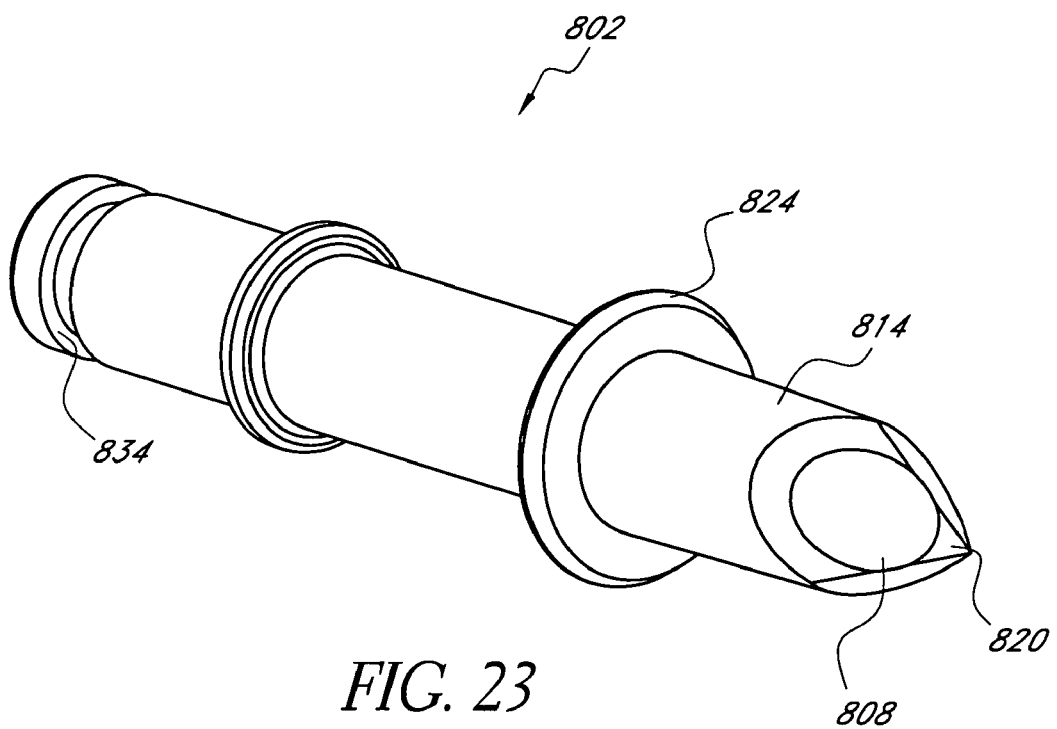
FIG. 23 is a perspective view of a cannula connector that is configured to pierce the membrane of the membrane assembly of FIG. 22.

In some applications, it is preferred that there not be a transition in the blood flow characteristics within the cannula connector 802. For example, it might be advantageous in some applications to provide a constant lumen size from the proximal end of the conduit 50, through the system 700, and to the distal end of the cannula 800. In other arrangements, it might be advantageous to provide only an increase in the lumen size between the cannula connector 802 and the distal end of the cannula 800. In such arrangements, the cannula connector 802 could be configured with a substantially constant cross-sectional area from its proximal end to its distal end. This arrangement is shown in FIGS. 18, 19, and 23.

In some priming techniques, discussed further below, it is beneficial to be able to selectively close a portion of a blood flow path. For example, the lumens at least partially defined in any of the cannula 800, the cannula connector 802, the conduit 50, and the tube connector 706 could selectively be closed to limit or prevent blood flow at least temporarily. In one technique discussed in more detail below, the transition section 816 is configured to be compressible such that the lumen in the transition section 816 can be selectively closed to blood-flow. As discussed further below, closing the lumen prevents an excessive amount of fluid to flow distal to proximal in the cannula 800. In a medical application, the distal end of the cannula 800 can be coupled with an artery under pressure prior to the system 700 being joined. Selective closing of the lumen 808 prevents excessive amounts of blood from being lost.

The piercing member 814 preferably is configured to pierce the membrane 718 upon joining the cannula connector 802 to the tube connector 706. For example, the piercing member 814 can be provided with a tip 820 that is configured such that will perforate the membrane 718 if the tip 820 is advanced toward the tube assembly 702. The tip 820 can be configured as a sharp surface or point. In one arrangement, the tip 820 is configured to be advanceable into the tube connector 706, for example by having an outer size that is slightly smaller than the inner size defined by the inner wall 734. In one arrangement, the tip 820 is configured with an inclined surface that matches the internal surface 732. The internal surface 732 can be made of a compressible or resilient material. When the tip 820 is advanced into engagement with the surface 732, the surface deforms such that few or no voids are located between the surface 732 and the tip 820. The elimination of voids between these structures reduces the likelihood that blood will escape from the priming system 700. Eliminating voids at the surface near the lumen near the surface also provides a seamless lumen for advantageous flow characteristics.

As discussed above, the system 700 advantageously minimizes or eliminates flow disruption to prevent damage to the fluid flowing in the system when the fluid is delicate. The system 700 can be configured with a structure to assist the user in coupling the tube connector 706 and the cannula connector 802. For example, in some arrangements where the surface 732 is compressible if the tip 820 is advanced to far relative to the tube connector 706, the surface 732 might be deformed into the blood flow path. This condition is sometimes referred to herein as "overinsertion." To prevent or minimize overinsertion, the system 700 can include a stop member 824. The stop member 824 can take any suitable form and can be located in any convenient location on the system. For example, the stop member 824 can be a shoulder on the cannula connector 802 that includes an annulus that contacts or abuts an end surface of the tube connector 706 when the cannula connector 802 is sufficiently, but not overly, inserted into the tube connector 706. This arrangement is illustrated in FIG. 17.

Rather than a shoulder, the stop member 824 can be configured as a ring or annulus mounted on an outer surface of the cannula connector 824, as illustrated in FIGS. 18, 19, and 23. The ring or annular arrangement functions in a similar fashion to the shoulder of FIG. 17. In particular, the cannula connector 802 can be advanced into the tube connector 706 until the ring or annulus configuration stop member 824 is in contact with an end surface of the tube connector 706. This condition is illustrated in FIG. 18. The location of the ring or annulus stop member is such that overinsertion will not occur.

In some applications, the system 700 can be coupled with a cannula by inserting the cannula connector 802 into a proximal end of the cannula. The cannula connector 802 can be configured to engage the proximal end of the cannula for such application. For example, one or a plurality of engagement features 834 can be provided near the distal end of the cannula connector 802. The engagement features 834 can be ridges extending outwardly from an outer surface of the cannula connector 802 near the distal end thereof. In another embodiment, the engagement feature 834 can be a recess into which a portion of a cannula 800 can subside when inserted over the distal end of the cannula connector 802.

In one embodiment, the priming system 700 includes a locking device 850 for securely connecting the tube assembly 702 and the cannula assembly 704 together. The locking device 850 can take any suitable form. In one embodiment one or more lateral extensions 852A are provided on the tube connector 706 and one or more lateral extensions 852B are provided on the cannula connector 802. The lateral extensions 852A, 852B are configured to have a force directed parallel to the longitudinal axis of the housing 708 applied thereto to prevent the connectors 706, 802 from becoming disengaged inadvertently. The force can be applied by a clamp or other suitable force generating device.

In another embodiment illustrated in FIG. 19, the locking device 850 comprises one or more prongs 856 provided on the end cap 738. The prongs 768 are configured to engage a portion of the cannula assembly 704 to lock the cannula assembly and the tube assembly 702 together. For example, the prongs 856 can be configured to engage the ring or annulus-type stop member 824 illustrated in FIG. 19. The engagement of the prongs with the member 824 can be provided by configuring the prongs to define an inner dimension that is slightly smaller than an outer dimension (e.g., the perimeter or circumference) of the stop member 824. Accordingly, when the stop member 824 is advanced past the distal ends of the prongs 856, the prongs are deflected laterally outwardly. In one embodiment, the prongs 856 have hook-like distal ends such that after then cannula connector 802 is sufficiently advanced the hook ends are distal of the stop member 824 and thereby prevent the stop member 824 from inadvertently being moved distally out of the tube connector 706.

The systems described above can be used in a method of priming a blood circuit that includes the pump 32, the inflow conduit 50 (or other pump tube) having a pump tube lumen fluidly coupled with the pump 32. The membrane 718, which is gas permeable, extends across the pump tube lumen 710. The system also includes the cannula 800 having a cannula lumen that extends between the first and second ends 804, 806. A piercing structure 814, which can include the tip 820, is adjacent to the first end 804. In one technique, a biocompatible liquid is forced into the pump tube lumen 710 at a location between the membrane 718 and the pump 34 to pressurize the pump tube lumen 710. The biocompatible liquid forces gas in the pump tube lumen 710 out of the lumen 710 through the membrane 718. Thus, the lumen 710 can be substantially purged of gas by the biocompatible liquid. Thereafter, the piercing structure 814 can be used to pierce the membrane 718 such that the cannula lumen 808 and the pump tube lumen 710 are in fluid communication.

In some arrangements and techniques, the pierced portion of the membrane 718 is forced between an outer wall of the cannula connector and the inner wall 734 of the housing 708 when the cannula connector is inserted into the pump tube connector 706. This arrangement and technique advantageously traps the membrane 718 out of the fluid flow path to prevent the introduction of the membrane or at least substantial, large portions thereof, from entering the flow. In some techniques, the piercing member 814 is configured so that upon connection, the membrane 718 is opened to create a flap that is substantially sandwiched between an outer wall of the cannula connector and the inner wall 734 of the pump tube connector 706.

In one arrangement and technique, the housing 708 is configured such that access to the third port 722 is blocked by an outer wall of the cannula connector 802 when the cannula connector is inserted into the pump tube connector 706. This advantageously prevents fluid in the fluid flow path from escaping through the third port 722 and also prevents contaminants from entering the blood flow path through the third port.

In one variation, the cannula lumen 808 is pressurized prior to piercing the membrane 718 such that a liquid in the cannula lumen flows out of the first end of the cannula lumen. As discussed above, the amount of liquid that flows out of the cannula lumen 808 can be limited by a clamp or other structure for selectively closing off the lumen. In some techniques, the presence of fluid in the lumen can be checked by loosening a clamping structure selectively applied to a portion of the cannula assembly 704. Permitting a small volume of fluid to escape from the proximal end of the cannula assembly 704 is one technique for eliminating gas from the cannula assembly. This technique generally is performed prior to connecting the tube assembly 702 and the cannula assembly 704 together.

In another technique, the cannula connector 802 and the pump tube connector 706 are locked together to prevent these structures from inadvertently becoming disengaged during the procedure, as discussed above.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

What is claimed is:

1. A system for priming a blood-flow circuit coupled with a pump, comprising:
   a pump tube assembly comprising a pump tube and a pump tube connector, the connector comprising a housing with a lumen therethrough having a housing cross-sectional area, the housing also comprising a first port, a membrane extending across the first port, a second port configured to couple with the pump tube, and a third port configured to couple with a source of biocompatible liquid; and
   a cannula assembly comprising:
   a cannula comprising a first end and a second end configured to couple with a blood vessel, the cannula defining a portion of a cannula lumen having a first cross-sectional area; and
   a cannula connector comprising a piercing member that defines a portion of the cannula lumen having a second cross-sectional area, the second cross-sectional area being substantially the same as the first cross-sectional area, the piercing member configured to pierce the membrane upon joining the cannula connector to the pump tube connector; and
   wherein the piercing member comprises a first surface and the pump tube connector comprises a second surface, the first and second surfaces configured to engage so as to provide a seamless lumen within the pump tube connector at least at the location where the first and second surfaces engage; and
   wherein the second surface is formed of a material that conforms to the first surface when the piercing member is fully inserted, whereby a seal is formed between the first and second surfaces.

2. The system of claim 1, wherein the material that forms the second surface comprises silicone.

3. The system of claim 1, wherein the membrane is permeable to gas.

4. The system of claim 1, further comprising a source of biocompatible liquid configured to couple with the third port.

5. The system of claim 4, wherein the biocompatible liquid comprises saline.

6. The system of claim 1, wherein the pierced portion of the membrane is forced between an outer wall of the cannula connector and an inner wall of the pump tube connector when the cannula connector is inserted into the pump tube connector.

7. The system of claim 1, wherein the piercing member is configured so that upon connection, the membrane is opened to create a flap that is substantially sandwiched between an outer wall of the cannula connector and an inner wall of the pump tube connector.

8. The system of claim 1, wherein the second end of the cannula is configured to fluidly couple with a blood vessel.

9. A system for priming a blood-flow circuit coupled with a pump, comprising:
   a pump tube assembly comprising a pump tube and a pump tube connector, the connector comprising a housing with a lumen therethrough having a housing cross-sectional area, the housing also comprising a first port, a membrane extending across the first port, a second port configured to couple with the pump tube, and a third port configured to couple with a source of biocompatible liquid; and
   a cannula assembly comprising:
   a cannula comprising a first end and a second end configured to couple with a blood vessel, the cannula defining a portion of a cannula lumen having a first cross-sectional area; and
   a cannula connector comprising a piercing member that defines a portion of the cannula lumen having a second cross-sectional area, the second cross-sectional area being substantially the same as the first cross-sectional area, the piercing member configured to pierce the membrane upon joining the cannula connector to the pump tube connector; and
   a clamp having a first configuration, wherein flow in the cannula lumen is completely stopped and a second configuration wherein a small amount of flow is permitted when the cannula lumen is pressurized.

10. The system of claim 9, wherein the second end of the cannula is configured to fluidly couple with a blood vessel.

11. A system for priming a blood-flow circuit coupled with a pump, comprising:
   a pump tube assembly comprising a pump tube and a pump tube connector, the connector comprising a housing with a lumen therethrough having a housing cross-sectional area, the housing also comprising a first port, a membrane extending across the first port, a second port configured to couple with the pump tube, and a third port configured to couple with a source of biocompatible liquid; and
   a cannula assembly comprising:
   a cannula comprising a first end and a second end configured to couple with a blood vessel, the cannula defining a portion of a cannula lumen having a first cross-sectional area; and
   a cannula connector comprising a piercing member that defines a portion of the cannula lumen having a second cross-sectional area, the second cross-sectional area being substantially the same as the first cross-sectional area, the piercing member configured to pierce the membrane upon joining the cannula connector to the pump tube connector; and wherein the membrane is permeable to gas; and wherein the membrane is formed of a high density fiber material.

12. The system of claim 11, wherein the high density fiber material comprises polyethylene.

13. The system of claim 11, wherein the second end of the cannula is configured to fluidly couple with a blood vessel.

14. A system for priming a blood-flow circuit coupled with a pump, comprising:

a pump tube assembly comprising a pump tube and a pump tube connector, the connector comprising a housing with a lumen therethrough having a housing cross-sectional area, the housing also comprising a first port, a membrane extending across the first port, a second port configured to couple with the pump tube, and a third port configured to couple with a source of biocompatible liquid; and a cannula assembly comprising:

a cannula comprising a first end and a second end configured to couple with a blood vessel, the cannula defining a portion of a cannula lumen having a first cross-sectional area; and a cannula connector comprising a piercing member that defines a portion of the cannula lumen having a second cross-sectional area, the second cross-sectional area being substantially the same as the first cross-sectional area, the piercing member configured to pierce the membrane upon joining the cannula connector to the pump tube connector; and wherein the housing is configured such that access to the third port is blocked by an outer wall of the cannula connector when the cannula connector is inserted into the pump tube connector.

15. The system of claim 14, wherein the second end of the cannula is configured to fluidly couple with a blood vessel.

16. A system for priming a blood-flow circuit coupled with a pump, comprising:

a pump tube assembly comprising a pump tube and a pump tube connector, the connector comprising a housing with a lumen therethrough having a housing cross-sectional area, the housing also comprising a first port, a membrane extending across the first port, a second port configured to couple with the pump tube, and a third port configured to couple with a source of biocompatible liquid; and a cannula assembly comprising:

a cannula comprising a first end and a second end configured to couple with a blood vessel, the cannula defining a portion of a cannula lumen having a first cross-sectional area; and a cannula connector comprising a piercing member that defines a portion of the cannula lumen having a second cross-sectional area, the second cross-sectional area being substantially the same as the first cross-sectional area, the piercing member configured to pierce the membrane upon joining the cannula connector to the pump tube connector; and further comprising a lock mechanism configured to securely attach the pump tube connector to the cannula connector.

17. The system of claim 16, wherein the second end of the cannula is configured to fluidly couple with a blood vessel.

18. A system for priming a blood-flow circuit coupled with a pump, comprising:

a pump tube assembly comprising a pump tube and a pump tube connector, the connector comprising a housing with a lumen therethrough having a housing cross-sectional area, the housing also comprising a first port, a membrane extending across the first port, a second port configured to couple with the pump tube, and a third port configured to couple with a source of biocompatible liquid; and a cannula assembly comprising:

a cannula comprising a first end and a second end configured to couple with a blood vessel, the cannula defining a portion of a cannula lumen having a first cross-sectional area; and a cannula connector comprising a piercing member that defines a portion of the cannula lumen having a second cross-sectional area, the second cross-sectional area being substantially the same as the first cross-sectional area, the piercing member configured to pierce the membrane upon joining the cannula connector to the pump tube connector; and further comprising a removable cap configured to be mounted to the housing and to hold the membrane across the first port.

19. The system of claim 18, wherein the second end of the cannula is configured to fluidly couple with a blood vessel.

20. A method of priming a blood circuit comprising a pump, a pump tube having a pump tube lumen fluidly coupled with the pump, a gas permeable membrane extending across the pump tube lumen, a cannula having a cannula lumen that extends between a first end and a second end, and a piercing structure adjacent to the first end, the method comprising:

forcing a biocompatible liquid into the pump tube lumen at a location between the gas permeable membrane and the pump to pressurize the pump tube lumen and to force gas in the pump tube lumen through the membrane;

piercing the membrane with the piercing structure such that the cannula lumen and the pump tube lumen are in fluid communication; and pressurizing the cannula lumen prior to piercing the membrane such that a liquid in the cannula lumen flows out of the first end of the cannula lumen.

21. A method of priming a blood circuit comprising a pump, a pump tube having a pump tube lumen fluidly coupled with the pump, a gas permeable membrane extending across the pump tube lumen, a cannula having a cannula lumen that extends between a first end and a second end, and a piercing structure adjacent to the first end, the method comprising:

forcing a biocompatible liquid into the pump tube lumen at a location between the gas permeable membrane and the pump to pressurize the pump tube lumen and to force gas in the pump tube lumen through the membrane;

piercing the membrane with the piercing structure such that the cannula lumen and the pump tube lumen are in fluid communication;

providing a pump tube connector in which the membrane is housed and a cannula connector comprising the piercing member;

attaching the pump tube connector to the pump tube;

attaching the cannula connector to the cannula.

22. The method of claim 21, further comprising locking the cannula connector to the pump tube connector.

23. A method of priming a blood circuit comprising a pump, a pump tube having a pump tube lumen fluidly coupled with the pump, a gas permeable membrane extending across the pump tube lumen, a cannula having a cannula lumen that extends between a first end and a second end, and a piercing structure adjacent to the first end, the method comprising:

forcing a biocompatible liquid into the pump tube lumen at a location between the gas permeable membrane and the pump to pressurize the pump tube lumen and to force gas in the pump tube lumen through the membrane;

piercing the membrane with the piercing structure such that the cannula lumen and the pump tube lumen are in fluid communication;

clamping the cannula between the distal end of the cannula and the cannula connector to limit flow of fluid in the cannula prior to pressurizing the lumen of the cannula; and permitting flow of liquid in the lumen of the cannula prior to piercing the membrane.

24. The method of claim 23, further comprising unclamping the cannula to permit fluid flow in the lumen of the cannula.

25. A method of priming a blood circuit comprising a pump, a pump tube having a pump tube lumen fluidly coupled with the pump, a gas permeable membrane extending across the pump tube lumen, a cannula having a cannula lumen that extends between a first end and a second end, and a piercing structure adjacent to the first end, the method comprising:

forcing a biocompatible liquid into the pump tube lumen at a location between the gas permeable membrane and the pump to pressurize the pump tube lumen and to force gas in the pump tube lumen through the membrane; and piercing the membrane with the piercing structure such that the cannula lumen and the pump tube lumen are in fluid communication; and wherein pressure in the pump tube lumen and the cannula lumen force all air in the lumens out of the blood circuit.

26. A connector system for use in priming a blood circuit having a pump, a conduit having a first end coupled with the pump and a second end, a cannula having a first end and a second end configured to fluidly couple with a blood vessel, and a cannula lumen extending therebetween, the system comprising:

a first connector configured to couple with the second end of the conduit, the first connector comprising a gas permeable membrane, a main lumen extending from the gas permeable membrane, and a secondary lumen having a first end configured to couple with a source of biocompatible liquid and a second end in fluid communication with the main lumen; and a second connector configured to couple with the first end of the cannula, the second connector having an end configured to be inserted through the gas permeable membrane into the first connector, whereby fluid communication can be established between the main lumen of the first connector and the cannula lumen; and wherein when the second connector is inserted into the first connector, the secondary lumen is blocked by the second connector.

27. The system of claim 26, wherein the first connector has an internal surface and the second connector has an end surface configured to engage with the internal surface of the first connector.

28. A connector system for use in priming a blood circuit having a pump, a conduit having a first end coupled with the pump and a second end, a cannula having a first end and a second end configured to fluidly couple with a blood vessel, and a cannula lumen extending therebetween, the system comprising:

a first connector configured to couple with the second end of the conduit, the first connector comprising a gas permeable membrane, a main lumen extending from the gas permeable membrane, and a secondary lumen having a first end configured to couple with a source of biocompatible liquid and a second end in fluid communication with the main lumen; and a second connector configured to couple with the first end of the cannula, the second connector having an end configured to be inserted through the gas permeable membrane into the first connector, whereby fluid communication can be established between the main lumen of the first connector and the cannula lumen; and wherein the first connector is configured such that the gas permeable membrane can be replaced to enable the connector system to be reused.

29. A connector system for use in priming a blood circuit having a pump, a conduit having a first end coupled with the pump and a second end, a cannula having a first end and a second end configured to fluidly couple with a blood vessel, and a cannula lumen extending therebetween, the system comprising:

a first connector configured to couple with the second end of the conduit, the first connector comprising a gas permeable membrane, a main lumen extending from the gas permeable membrane, and a secondary lumen having a first end configured to couple with a source of biocompatible liquid and a second end in fluid communication with the main lumen;

a second connector configured to couple with the first end of the cannula, the second connector having an end configured to be inserted through the gas permeable membrane into the first connector, whereby fluid communication can be established between the main lumen of the first connector and the cannula lumen; and a removable cap configured to be mounted to the first connector and to hold the membrane across the main lumen.

* * * * *